United States Patent
Gebert-Schwarzwaelder et al.

(10) Patent No.: US 9,889,321 B2
(45) Date of Patent: Feb. 13, 2018

(54) AGENTS FOR DYEING KERATIN FIBERS, CONTAINING AT LEAST ONE DIMERIC, RING-BRIDGED AZO DYE

(71) Applicant: Henkel AG & Co. KGaA, Duesseldorf (DE)

(72) Inventors: Antje Gebert-Schwarzwaelder, Neuss (DE); Helmut Giesa, Meerbusch (DE); Melanie Moch, Dormagen (DE)

(73) Assignee: Henkel AG & Co. KGaA, Deusseldorf (DE)

( * ) Notice: Subject to any disclaimer, the term of this patent is extended or adjusted under 35 U.S.C. 154(b) by 0 days.

(21) Appl. No.: 15/528,532

(22) PCT Filed: Oct. 14, 2015

(86) PCT No.: PCT/EP2015/073776
§ 371 (c)(1),
(2) Date: May 22, 2017

(87) PCT Pub. No.: WO2016/083013
PCT Pub. Date: Jun. 2, 2016

(65) Prior Publication Data
US 2017/0266468 A1   Sep. 21, 2017

(30) Foreign Application Priority Data

Nov. 25, 2014  (DE) .................. 10 2014 223 937

(51) Int. Cl.
*A61Q 5/10* (2006.01)
*A61Q 5/06* (2006.01)
*A61K 8/49* (2006.01)

(52) U.S. Cl.
CPC .............. *A61Q 5/065* (2013.01); *A61K 8/496* (2013.01); *A61K 8/4966* (2013.01); *A61K 2800/4322* (2013.01)

(58) Field of Classification Search
CPC ...... A61Q 5/065; A61K 8/496; A61K 8/4966; A61K 2800/4322
See application file for complete search history.

(56) References Cited

U.S. PATENT DOCUMENTS

| 4,562,249 | A | 12/1985 | Schwander et al. |
| 4,563,191 | A * | 1/1986 | Hahnke .................. C09B 69/001 264/78 |
| 4,607,071 | A | 8/1986 | Haehnke et al. |
| 7,407,516 | B2 | 8/2008 | Vidal |
| 2001/0001333 | A1 | 5/2001 | Samain |
| 2004/0200009 | A1 | 10/2004 | Vidal |
| 2004/0244124 | A1 | 12/2004 | Plos et al. |
| 2005/0235433 | A1 | 10/2005 | Rondeau |
| 2006/0112502 | A1 | 6/2006 | Cotteret et al. |
| 2012/0325261 | A1 | 12/2012 | Hashimoto et al. |

| 2014/0101868 | A1 | 4/2014 | Hoffmann et al. |
| 2014/0165301 | A1 | 6/2014 | Schweinsberg et al. |
| 2014/0289970 | A1 | 10/2014 | Gross et al. |

FOREIGN PATENT DOCUMENTS

| CA | 2303209 | A1 | 3/1999 |
| DE | 2822912 | A1 | 11/1979 |
| DE | 4128490A | A1 | 3/1993 |
| EP | 0531943 | A1 | 3/1993 |
| EP | 1609456 | A1 | 12/2005 |
| EP | 1483334 | B1 | 7/2007 |
| EP | 1448156 | B1 | 8/2007 |
| FR | 2915681 | A1 | 11/2008 |
| GB | 910121 | A | 11/1962 |
| GB | 1186753 | A | 4/1970 |
| GB | 1189753 | A | 4/1970 |
| WO | 02100369 | A2 | 12/2002 |

OTHER PUBLICATIONS

STIC Search Report dated Jun. 28, 2017.*
EPO, International Search Report and Written Opinion issued in International Application No. PCT/EP2015/073776 dated Nov. 30, 2015.
EPO, International Search Report and Written Opinion issued in International Application PCT/EP2015/072773, dated Nov. 12, 2015.
Preliminary Amendment for U.S. Application entitled "Agents for Dyeing Keratin Fibers, Containing at Least One Dimeric, Dicationic Azo Dye and at Least One Anionic Surfactant".
Substitute Specification for U.S. Application entitled "Agents for Dyeing Keratin Fibers, Containing at Least One Dimeric, Dicationic Azo Dye and at Least One Anionic Surfactant".
EPO, International Search Report and Written Opinion issued in International Application PCT/EP2015/072774, dated Nov. 23, 2015.

(Continued)

*Primary Examiner* — Eisa B Elhilo
(74) *Attorney, Agent, or Firm* — Lorenz & Kopf, LLP

(57) ABSTRACT

The present disclosure relates to agents for dyeing keratin fibers, in particular human hair, containing, in a cosmetic carrier (a) at least one direct dye of formula (I), wherein Het 1, Het 2 represent a cationic heterocycle, and A1, A2, independently of one another, represent a grouping of formulas (VIII) or (IX), wherein n represents a whole number of between 2-6, and m, p, independently of one another, represent the numbers 2 or 3.

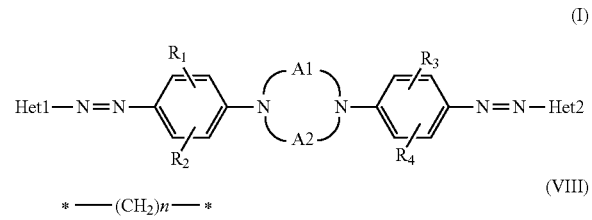

20 Claims, No Drawings

(56) References Cited

OTHER PUBLICATIONS

Preliminary Amendment for U.S. Application entitled "Agents for Dyeing Keratin Fibers, Containing at Least One Dimeric, Dicationic Azo Dye and at Least One Non-Ionic Surfactant".
Substitue Specification for U.S. Application entitled "Agents for Dyeing Keratin Fibers, Containing at Least One Dimeric, Dicationic Azo Dye and at Least One Non-Ionic Surfactant".
EPO, International Search Report and Written Opinion issued in International Application PCT/EP2015/073775, dated Dec. 1, 2015.
Preliminary Amendment for U.S. Application entitled "Agents for Dyeing Keratin Fibers, Containing at Least One Dimeric, Dicationic Azo Dye and at Least One Anionic and/or Cationic Surfactant".
Substitute Specification for U.S. Application entitled "Agents for Dyeing Keratin Fibers, Containing at Least One Dimeric, Dicationic Azo Dye and at Least One Anionic and/or Cationic Surfactant".
EPO, International Search Report and Written Opinion issued in International Application No. PCT/EP2015/073779, dated Nov. 30, 2015.
Preliminary Amendment for U.S. Application entitled "Agents for Dyeing Keratin Fibres, Containing at Least One Dimeric, Dicationic Azo Dye With Special Substitution Pattern".
Substitute Specification for U.S. Application entitled "Agents for Dyeing Keratin Fibres, Containing at Least One Dimeric, Dicationic Azo Dye With Special Substitution Pattern".
USPTO, Office Action in U.S. Appl. No. 15/528,529 dated Aug. 31, 2017.
USPTO, Office Action in U.S. Appl. No. 15/528,538 dated Aug. 30, 2017.
USPTO, Office Action in U.S. Appl. No. 15/528,539 dated Aug. 31, 2017.
USPTO, Office Action in U.S. Appl. No. 15/528,530 dated Aug. 31, 2017.
STIC Search Report dated Jul. 29, 2017 (U.S. Appl. No. 15/528,529).
STIC Search Report dated Jul. 2, 2017 (U.S. Appl. No. 15/528,538).
STIC Search Report dated Aug. 6, 2017 (U.S. Appl. No. 15/528,539).
STIC Search Report dated Aug. 1, 2017 (U.S. Appl. No. 15/528,530).

* cited by examiner

AGENTS FOR DYEING KERATIN FIBERS, CONTAINING AT LEAST ONE DIMERIC, RING-BRIDGED AZO DYE

CROSS-REFERENCE TO RELATED APPLICATIONS

This application is a U.S. National-Stage entry under 35 U.S.C. § 371 based on International Application No. PCT/EP2015/073776, filed Oct. 14, 2015, which was published under PCT Article 21(2) and which claims priority to German Application No. 10 2014 223 937.0, filed Nov. 25, 2014, which are all hereby incorporated in their entirety by reference.

TECHNICAL FIELD

The present disclosure relates to agents for dyeing keratin fibers, particularly human hairs, which contain (a) at least one dimeric, ring-bridged azo dye of a special formula (I).

BACKGROUND

In general, either direct dyes or oxidation dyes are used to color keratin fibers. With oxidation dyes, while intense colorations with good fastness characteristics can be achieved, the color is generally developed under the influence of oxidizing agents such as $H_2O_2$, for example, which can result in the damaging of the fibers in many cases. Moreover, many oxidation dye precursors or certain mixtures of oxidation dye precursors can have a sensitizing effect on people with sensitive skin. Direct dyes are applied under gentler conditions. Their disadvantage lies in the fact that the colorations often have only inadequate fastness characteristics.

A person skilled in the art will use direct dyes of different dye classes depending on the desired coloration result. The direct dyes known from the prior art belong, for example, to the class of nitro dyes, anthraquinone dyes, azo dyes, triarylmethane dyes, or methine dyes. All of these dye classes must satisfy a certain series of requirements in order to be used in the area of cosmetics. For instance, direct dyes should yield an intense coloring result and have fastness characteristics that are as good as possible. The coloration result obtained with direct dyes should be affected as little as possible by environmental influences that is, the dyes should have good wash fastness, light fastness, and rub fastness. Chemical influences to which the keratin fibers may be exposed after the dyeing process (such as permanent waves, for example) should also alter the coloration result as little as possible.

In order to also achieve lightening with the coloration at the same time, the direct dyes should, if possible, also be compatible with the oxidizing agents usually used in blonding processes (such as hydrogen peroxide and/or persulfates, for example).

For more pronounced lightening of dark hair, not only hydrogen peroxide alone, but a combination of hydrogen peroxide and persulfates (e.g., ammonium persulfate, potassium persulfate, and/or sodium persulfate) is used. So, if dark hair is to be dramatically lightened and simultaneously colored in a bright tone, it is advantageous to use a mixture of hydrogen peroxide, persulfates, and a direct dye. Although many intensively coloring direct dyes for dyeing hair are known to a person skilled in the art, he is familiar with only a very limited selection of dyes that can withstand the strong oxidative conditions such as those created through the mixing of the abovementioned oxidizing agents. What is more, the oxidation-stable dyes known from the prior art have serious drawbacks in terms of their fastness characteristics.

A need therefore continues to exist for dyes that are highly stable in the presence of strong oxidizing agents in order to enable the simultaneous dyeing and pronounced lightening of hair. Even under these extreme conditions of use, these dyes must not lose their positive fastness and coloring characteristics.

It has been found that bright and intense colorations can be produced using cationic direct dyes in particular. Cationic dyes are often characterized by an especially high affinity for keratin fibers, which can be attributed to the interactions of the positive charges of the dyes with negatively charged structural components of the keratin fibers. This is why it is often possible to achieve especially intense colorations using cationic dyes.

Two examples of monomeric cationic azo dyes that are sufficiently known from the prior art are Basic Orange 31 (alternative name: 2-[(4-aminophenyl)azo]-1,3-dimethyl-1H-imidazolium chloride, CAS no. 97404-02-9) and Basic Red 51 (alternative name: 2-[((4-dimethylamino)phenyl)azo]-1,3-dimethyl-1H-imidazolium chloride, CAS no. 77061-58-6).

Both dyes color keratin fibers with outstanding color intensity in the orange to red nuance range. Moreover, a need also continues to exist for direct blue dyes that are optimally compatible with these two dyes.

BRIEF SUMMARY

Agents for dyeing keratin fibers are provided herein. In an exemplary embodiment, an agent for dyeing keratinic fibers includes, in a cosmetic carrier, (a) at least one direct dye of formula (I),

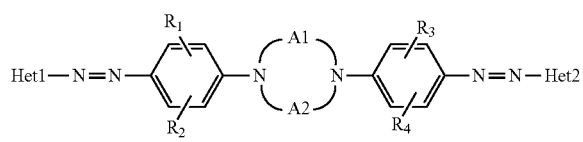

where
Het 1, Het 2 independently of one another, stand for one of the structures (II), (III), (IV), (V), (VI), or (VII),

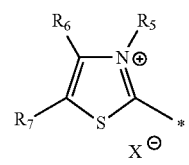

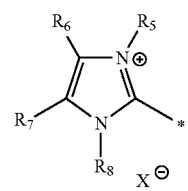

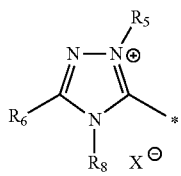
(IV)

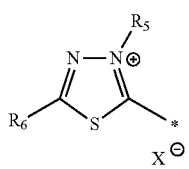
(V)

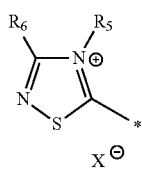
(VI)

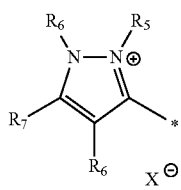
(VII)

$R^1$, $R^3$ independently of one another, stand for a hydrogen atom, a $C_1$-$C_6$ alkyl group, a halogen atom from the group of chlorine, bromine, fluorine, or iodine, for a $C_1$-$C_6$ alkoxy group, or for a nitro group, $R^2$, $R^4$ independently of one another, stand for a hydrogen atom, a $C_1$-$C_6$ alkyl group, a halogen atom from the group of chlorine, bromine, fluorine, or iodine, for a $C_1$-$C_6$ alkoxy group, or for a nitro group, $R^5$, $R^8$ each independently of one another, stand for a $C_1$-$C_6$ alkyl group or for a $C_2$-$C_6$ alkenyl group, $R^6$, $R^7$ each independently of one another, stand for a hydrogen atom, a $C_1$-$C_6$ alkyl group, a halogen atom from the group of chlorine, bromine, fluorine, or iodine, for a $C_1$-$C_6$ alkoxy group, or for a nitro group, A1, A2 independently of one another, stand for a grouping of the formulas (VIII) or (IX),

*—(CH$_2$)$n$-*   (VIII)

*—(CH$_2$)$m$-O—(CH$_2$)$p$-*   (IX)

n stands for an integer from 2 to 6, m, p each independently of one another, stand for the numbers 2 or 3, X— stands for a physiologically acceptable anion, chloride, bromide, iodide, methyl sulfate, methyl sulfonate, p-toluene sulfonate, acetate, hydrogen sulfate, ½ sulfate, or ½ tetrachlorozincate.

DETAILED DESCRIPTION

The following detailed description is merely exemplary in nature and is not intended to limit the present disclosure or the application and uses of the subject matter as described herein. Furthermore, there is no intention to be bound by any theory presented in the preceding background or the following detailed description.

It is therefore the object of the present application to provide colorants for keratin fibers, particularly human hairs, that have good technical application characteristics in terms of depth of color and fastness characteristics, such as light, rub, and wash fastness, as well as fastness to perspiration and cold waves. When used simultaneously with oxidation dyes and/or oxidizing agent, the direct dyes are to have a high level of stability in the presence of hydrogen peroxide and other oxidizing agent and not lose their positive fastness and dyeing characteristics. In addition, colorations are to be achieved that are as bright and intense as possible.

Furthermore, the aforementioned dyes are to also have especially good compatibility with the cationic azo dyes Basic Orange 31 and Basic Red 51.

It was found that the application of dimeric dicationic azo dyes of the general formula (I) in cosmetic dyeing agents to keratin fibers results in especially intense and bright colorations.

A first object of the present disclosure is an agent for coloring keratin fibers, particularly human hairs, containing in a cosmetic carrier (a) at least one direct dye of formula (I),

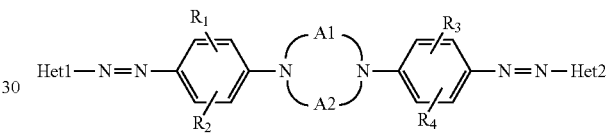
(I)

where

Het 1, Het 2 independently of one another, stand for one of the structures (II), (III), (IV), (V), (VI), or (VII),

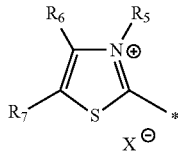
(II)

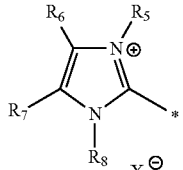
(III)

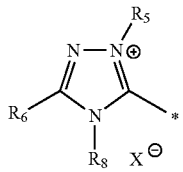
(IV)

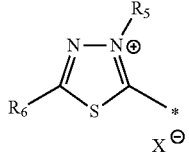
(V)

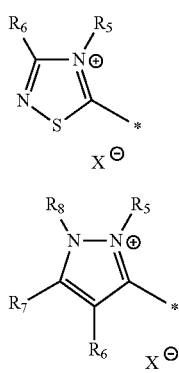

(VI)

(VII)

R¹, R³ independently of one another, stand for a hydrogen atom, a $C_1$-$C_6$ alkyl group, a halogen atom from the group of chlorine, bromine, fluorine, or iodine, for a $C_1$-$C_6$ alkoxy group, or for a nitro group,
R², R⁴ independently of one another, stand for a hydrogen atom, a $C_1$-$C_6$ alkyl group, a halogen atom from the group of chlorine, bromine, fluorine, or iodine, for a $C_1$-$C_6$ alkoxy group, or for a nitro group,
R⁵, R⁸ each independently of one another, stand for a $C_1$-$C_6$ alkyl group or for a $C_2$-$C_6$ alkenyl group,
R⁶, R⁷ each independently of one another, stand for a hydrogen atom, a $C_1$-$C_6$ alkyl group, a halogen atom from the group of chlorine, bromine, fluorine, or iodine, for a $C_1$-$C_6$ alkoxy group, or for a nitro group,
A1, A2 independently of one another, stand for a grouping of the formulas (VIII) or (IX),

 (VIII)

 (IX)

n stands for an integer from 2 to 6,
m, p each independently of one another, stand for the numbers 2 or 3,
X— stands for a physiologically acceptable anion, preferably from the group of chloride, bromide, iodide, methyl sulfate, methyl sulfonate, p-toluene sulfonate, acetate, hydrogen sulfate, ½ sulfate, or ½ tetrachlorozincate.

Keratinic fibers, keratin-containing fibers or keratin fibers are to be understood as furs, wool, feathers and, particularly, human hair. Even though the agents according to the present disclosure are suitable first and foremost for lightening keratin fibers, there is nothing in principle to prevent them from being used in other areas as well.

The term "dyeing of keratin fibers" used according to the present disclosure includes any and all forms of the dyeing of fibers. In particular, it includes the changes in color that call under the terms tinging, blonding, mattifying, oxidative dyeing, semipermanent dyeing, permanent dyeing, and temporary dyeing. According to the present disclosure, changes in color that result in a lighter coloration result in comparison to the initial color, such as coloring blonding, for example, are also explicitly included. Coloring blonding is understood as the simultaneous lightening and dyeing of the keratin fibers, which can be achieved through the simultaneous use of oxidizing agent and dye in the dyeing agent.

The agents according to the present disclosure contain the direct dyes of formula (I) in a cosmetic carrier. This cosmetic carrier is preferably aqueous, alcoholic, or aqueous alcoholic. For the purpose of treating the hair, such carriers can be creams, emulsions, gels or even surfactant-containing foaming solutions such as shampoos, foaming aerosols, foam formulations, or other preparations, for example, that are suitable for use on the hair. It is also possible, however, to provide the formulation in powder or also tablet form for storage. Before application, it is then mixed in an aqueous solvent or with organic solvents or with mixtures of water and organic solvents in order to obtain the application mixture. In terms of the present disclosure, an aqueous carrier contains at least about 40 wt %, particularly at least about 50 wt % water. In terms of the present disclosure, aqueous alcoholic carriers are water-containing compositions which contain about 3 to about 70 wt % of a $C_1$-$C_4$ alcohol, particularly ethanol or isopropanol. The agents according to the present disclosure can additionally contain other organic solvents such as, for example, 4-methoxybutanol, ethyl diglycol, 1,2-propylene glycol, n-propanol, n-butanol, n-butylene glycol, glycerin, diethylene glycol monoethyl ether, and diethylene glycol mono-n-butyl ether. All are preferably water-soluble organic solvents. Preferred agents according to the present disclosure are characterized in that they additionally contain a nonaqueous solvent, with preferred agents according to the present disclosure containing the solvent in a concentration of about 0.1 to about 30 wt %, preferably in a concentration of about 1 to about 20 wt %, very especially preferably in a concentration of about 2 to about 10 wt %, each with respect to the agent.

The agents according to the present disclosure contain at least one direct dye of formula (I) as the essential ingredient (a).

The substituents $R^1$ to $R^8$ of the compounds of formula (I) are elucidated below for the sake of example: Examples of a $C_1$-$C_6$ alkyl group are the groups methyl, ethyl, propyl, isopropyl, n-butyl, s-butyl, and t-butyl, n-pentyl, and n-hexyl. Propyl, ethyl and methyl are preferred alkyl residues. Examples of a $C_2$-$C_6$ alkenyl group are vinyl, allyl, but-2-enyl, but-3-enyl, and isobutenyl, and preferred $C_2$-$C_6$ alkenyl residues are vinyl and allyl. Halogen atoms are selected from the group of chlorine, bromine, fluorine, and/or iodine, with chlorine and bromine being especially preferred. Examples of a $C_1$-$C_6$ alkoxy group are the methoxy, ethoxy, and propoxy group. A nitro group is to be understood as an —$NO_2$ grouping.

Every direct dye of formula (I) bears two cationic, heterocyclic terminal groups Het 1 and Het 2 which, independently of one another, can be selected from among the groupings of formulas (II) to (VII)

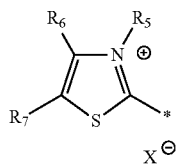 (II)

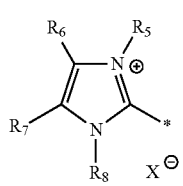 (III)

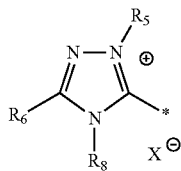
(IV)

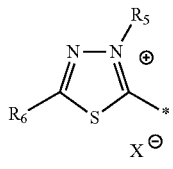
(V)

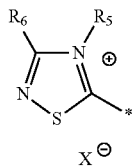
(VI)

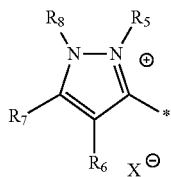
(VII)

Formula (II) represents a cationic thiazolium terminal group.

Formula (III) represents a cationic imidazolium terminal group. Formula (IV) represents a cationic 1,2,4-triazolium terminal group.

Formula (V) represents a cationic 1,3,4-thiadiazolium terminal group. Formula (VI) represents a cationic 1,2,4-thiadiazolium terminal group. Formula (VII) represents a cationic pyrazolium terminal group.

In each of formulas (II) to (VII), a position is marked with a star which indicates the attachment site of the heterocyclic terminal group Het 1 or Het 2 to the azo group in formula (I).

The heterocyclic terminal groups Het 1 and Het 2 in the dyes of formula (I) can be the same or different. Purer dyes are obtained if Het 1 and Het 2 are the same in a dye of formula (I).

The absorption spectrum of the dye—and hence the coloring of the dye as well—can be influenced through the selection of different terminal groups Het 1 and Het 2.

If intense colorations in the blue-violet range and particularly in the blue range are desired, it is advantageous if Het 1 and Het 2 stand for heterocyclic terminal groups of formula (II).

In contrast, if brilliant colorations in the red range are to be achieved, it is preferred if Het 1 and Het 2 are selected from the heterocyclic terminal groups of formulas (III) and/or (IV).

Moreover, especially pure and bright tones can be produced using dyes of formula (I) in which Het 1 and Het 2 stand for a group selected from among formulas (II), (III), or (IV). For this reason, it is especially preferred if the agent (a) according to the present disclosure contains at least one direct dye of the general formula (I), in which Het 1 and Het 2, independently of one another, stand for one of the structures (II), (III), or (IV)

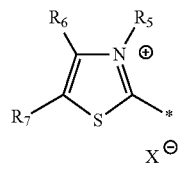
(II)

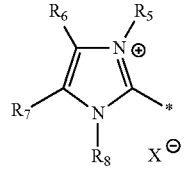
(III)

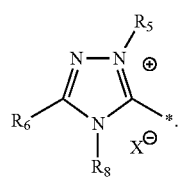
(IV)

In an especially preferred embodiment, an agent according to the present disclosure is characterized in that it (a) contains at least one direct dye of the general formula (I), in which Het 1, Het 2, independently of one another, stand for one of the structures (II), (III), or (IV)

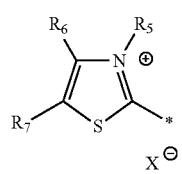
(II)

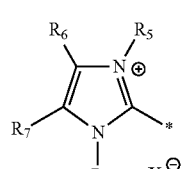
(III)

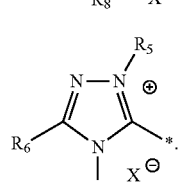
(IV)

In formula (I), the residues $R^1$ to $R^4$ indicate the substituent on the two phenyl rings of the direct dye.

Here, $R^1$, $R^3$, independently of one another, can stand for a hydrogen atom, a $C_1$-$C_6$ alkyl group, a halogen atom from the group of chlorine, bromine, fluorine, or iodine, for a $C_1$-$C_6$ alkoxy group, or for a nitro group. In principle, $R^1$ and $R^3$ in the dye of formula (I) can be the same or different. It is preferred, however, if $R^1$ and $R^3$ are the same in each dye of formula (I).

In an especially preferred embodiment, an agent according to the present disclosure is characterized in that it (a) contains at least one direct dye of the general formula (I), in which $R^1$, $R^3$ independently of one another, stand for a hydrogen atom, a $C_1$-$C_6$ alkyl group, or for a $C_1$-$C_6$ alkoxy group.

The residues $R^2$, $R^4$, independently of one another, can stand for a hydrogen atom, a $C_1$-$C_6$ alkyl group, a halogen atom from the group of chlorine, bromine, fluorine, or iodine, for a $C_1$-$C_6$ alkoxy group, or for a nitro group. In principle, $R^2$ and $R^4$ in the dye of formula (I) can be the same or different. It is preferred, however, if $R^2$ and $R^4$ are the same in each dye of formula (I).

In an especially preferred embodiment, an agent according to the present disclosure is characterized in that it (a) contains at least one direct dye of the general formula (I), in which $R^2$, $R^4$, independently of one another, stand for a hydrogen atom, a $C_1$-$C_6$ alkyl group, or for a $C_1$-$C_6$ alkoxy group, especially preferably for a hydrogen atom.

In a very especially preferred embodiment, an agent according to the present disclosure is therefore characterized in that it (a) contains at least one direct dye of the general formula (I), in which
$R^1$ stands for a hydrogen atom, for a methyl group, or for a methoxy group,
$R^2$ stands for a hydrogen atom,
$R^3$ stands for a hydrogen atom, for a methyl group, or for a methoxy group, and
$R^4$ stands for a hydrogen atom.

The heterocyclic terminal groups Het 1 and Het 2 of formulas (II) to (VII) bear the residues $R^5$, $R^6$, $R^7$, and/or $R^8$.

The residues $R^5$ and $R^8$ are each bonded to an N atom of the heterocyclic terminal group. Here, the residues $R^5$ and $R^8$, each independently of one another, can stand for a $C_1$-$C_6$ alkyl group or for a $C_2$-$C_6$ alkenyl group. It is preferred if $R^5$ and $R^8$, independently of one another, stand for a $C_1$-$C_6$ alkyl group, especially preferably for a methyl group or an ethyl group.

The residues $R^6$ and $R^7$, each independently of one another, can stand for a hydrogen atom, a $C_1$-$C_6$ alkyl group, a halogen atom from the group of chlorine, bromine, fluorine, or iodine, for a $C_1$-$C_6$ alkoxy group, or for a nitro group. It is preferred if $R^8$ and $R^9$, independently of one another, stand for a hydrogen atom, a $C_1$-$C_6$ alkyl group, or for a $C_1$-$C_6$ alkoxy group.

In another especially preferred embodiment, an agent according to the present disclosure is therefore characterized in that it (a) contains at least one direct dye of the general formula (I), in which
$R^5$, $R^8$ each independently of one another, stand for a $C_1$-$C_6$ alkyl group, and
$R^6$, $R^7$ each independently of one another, stand for a hydrogen atom, a $C_1$-$C_6$ alkyl group, or for a $C_1$-$C_6$ alkoxy group.

In a very especially preferred embodiment, an agent according to the present disclosure is therefore characterized in that it (a) contains at least one direct dye of the general formula (I), in which
$R^5$, $R^8$ each independently of one another, stand for a $C_1$-$C_6$ alkyl group, and
$R^6$, $R^7$ each independently of one another, stand for a hydrogen atom or for a $C_1$-$C_6$ alkyl group.

The inventive dimeric direct dyes of the general formula (I) further comprise the groupings A1 and A2. The two groupings A1 and A2 are each joined with the two nitrogen atoms, which are bonded to the two phenyl groups of formula (I). Together with the two nitrogen atoms, the two groupings A1 and A2 thus form a heterocycle. The two groupings A1, A2, independently of one another, stand for a grouping of formula (VIII) or (IX).

$$*-(CH_2)n-* \qquad (VIII)$$

$$*-(CH_2)m-O-(CH_2)p-* \qquad (IX)$$

In formula (VIII), n stands for an integer from 2 to 3.

In formula (IX), m and p, independently of one another, stand for the number 2 or 3.

Especially intense colorations were able to be obtained using a direct dye of general formula (I) in which A1 and A2 both stand for a grouping of formula (VIII), with n standing for the number 2 or 3, especially preferably for the number 2.

In an especially preferred embodiment, an agent according to the present disclosure is therefore characterized in that it (a) contains at least one direct dye of the general formula (I), in which
A1, A2 both stand for a grouping of formula (VIII), $$*-(CH_2)n-* \qquad (VIII),$$

where
n stands for the number 2 or 3, preferably for the number 2.

In principle, A1 and A2 can be the same or different in each direct dye of formula (I); preferably, however, A1 and A2 are the same in each direct dye of formula (I).

If A1 and A2 each stand for a grouping of formula (VIII), where n is equal to 2, then the bridging moiety of A1, A2 and the two N atoms are a piperazine group. Dyes of formula (I) possessing a piperazine group as a heterocyclic linking moiety exhibit an especially good color-lifting capability on the keratin fibers.

The inventive dyes of formula (I) are dimeric azo dyes that are doubly positively charged. The two positive charges are each neutralized by the anionic counterion X (of the structural units (II) to (VII)). Here, it is the dicationic organic portion that is responsible for the dyeing of the keratin fibers. The counterions X serve merely to preserve electroneutrality, so that the exact nature of the counterions X plays no essential role in achieving the desired coloration result. Since the dye is used in a cosmetic agent, the counterions X must be physiologically acceptable. In this context, physiologically acceptable means suitable for use in the cosmetic agent (i.e., for application to human hair and human skin). The counterions X are each physiologically acceptable anions, preferably from the group chloride, bromide, iodide, methyl sulfate, methyl sulfonate, p-toluene sulfonate, acetate, hydrogen sulfate, ½ sulfate, or ½ tetrachlorozincate.

Chloride is understood as being a $Cl^-$ anion. Bromide is understood as being a $Br^-$ anion. Iodide is understood as being a $J^-$ anion. Methyl sulfate is understood as being an $H_3COSO_4^-$ anion.

Methyl sulfonate is understood as being an $H_3CSO_3^-$ anion. p-toluene sulfonate is understood as being an $H_3C(C_6H_4)SO_3^-$ anion. Acetate is understood as being an $H_3CCOO^-$ anion. Hydrogen sulfate is understood as being an $HSO_4^-$ anion. ½ sulfate is understood as being a half-equivalent of the doubly negatively charged $SO_4^{2-}$ anion. ½ tetrachlorozincate is understood as being a half-equivalent of the doubly negatively charged $ZnCl_4^{2-}$ anion. In the case of sulfate and tetrachlorozincate, it is therefore likewise possible and in keeping with the present disclosure if the dicationic dye of formula (I) is neutralized by an $SO_4^{2-}$ ion or by a $ZnCl_4^{2-}$ ion.

For reasons of synthetic accessibility, it is preferred if the two X— counterions of the structural units Het 1 and Het 2 are the same.

In another preferred embodiment, an agent for dyeing keratin fibers is characterized in that it contains at least one compound of the general formula (I) that is selected from among salts of 3-methyl-2-{2-[4-(4-{4-[2-(3-methyl-1,3-thiazol-3-ium-2-yl)diazen-1-yl]phenyl}piperazin-1-yl)phenyl]diazen-1-yl}-1,3-thiazol-3-ium

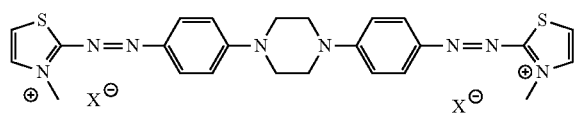

salts of 3-ethyl-2-{2-[4-(4-{4-[2-(3-ethyl-1,3-thiazol-3-ium-2-yl)diazen-1-yl]phenyl}piperazin-1-yl)phenyl]diazen-1-yl}-1,3-thiazol-3-ium

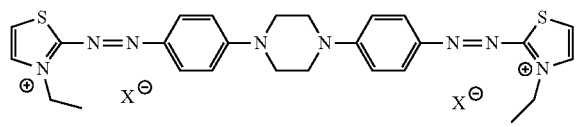

salts of 3-methyl-2-{2-[3-methyl-4-(4-{2-methyl-4-[2-(3-methyl-1,3-thiazol-3-ium-2-yl)diazen-1-yl]phenyl}piperazin-1-yl)phenyl]diazen-1-yl}-1,3-thiazol-3-ium

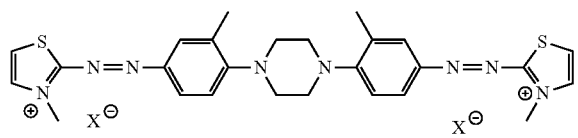

salts of 3-ethyl-2-{2-[4-(4-{4-[2-(3-ethyl-1,3-thiazol-3-ium-2-yl)diazen-1-yl]-2-methylphenyl}piperazin-1-yl)-3-methylphenyl]diazen-1-yl}-1,3-thiazol-3-ium

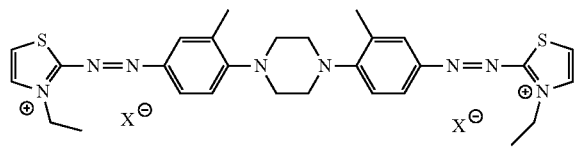

salts of 3-methyl-2-{2-[2-methyl-4-(4-{3-methyl-4-[2-(3-methyl-1,3-thiazol-3-ium-2-yl)diazen-1-yl]phenyl}piperazin-1-yl)phenyl]diazen-1-yl}-1,3-thiazol-3-ium

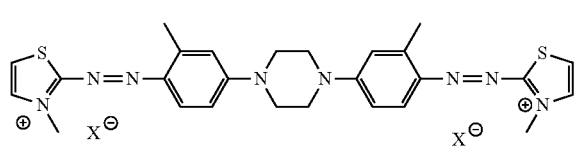

salts of 3-ethyl-2-{2-[4-(4-{4-[2-(3-ethyl-1,3-thiazol-3-ium-2-yl)diazen-1-yl]-3-methylphenyl}piperazin-1-yl)-2-methylphenyl]diazen-1-yl}-1,3-thiazol-3-ium

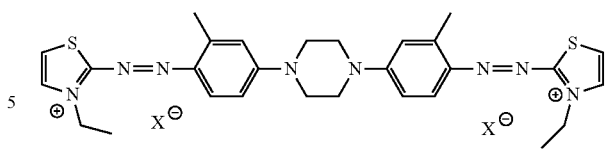

salts of 2-{2-[3-methoxy-4-(4-{2-methoxy-4-[2-(3-methyl-1,3-thiazol-3-ium-2-yl)diazen-1-yl]phenyl}piperazin-1-yl)phenyl]diazen-1-yl}-3-methyl-1,3-thiazol-3-ium

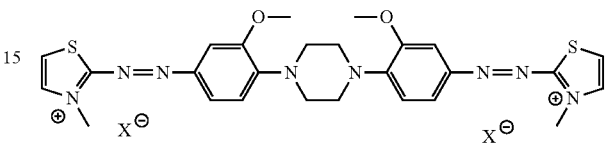

salts of 3-ethyl-2-{2-[4-(4-{4-[2-(3-ethyl-1,3-thiazol-3-ium-2-yl)diazen-1-yl]-2-methoxyphenyl}piperazin-1-yl)-3-methoxyphenyl]diazen-1-yl}-1,3-thiazol-3-ium

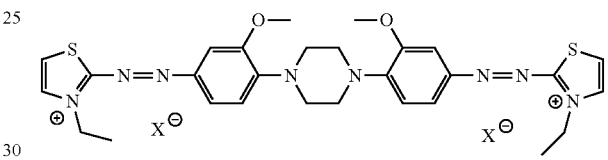

salts of 2-{2-[2-methoxy-4-(4-{3-methoxy-4-[2-(3-methyl-1,3-thiazol-3-ium-2-yl)diazen-1-yl]phenyl}piperazin-1-yl)phenyl]diazen-1-yl}-3-methyl-1,3-thiazol-3-ium

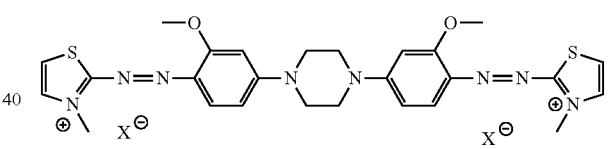

salts of 3-ethyl-2-{2-[4-(4-{4-[2-(3-ethyl-1,3-thiazol-3-ium-2-yl)diazen-1-yl]-3-methoxyphenyl}piperazin-1-yl)-2-methoxyphenyl]diazen-1-yl}-1,3-thiazol-3-ium

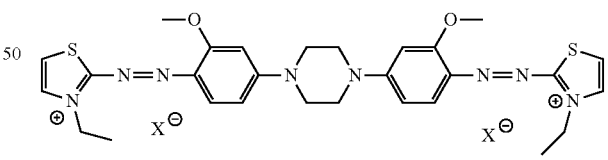

salts of 2-{2-[4-(4-{2,5-dimethyl-4-[2-(3-methyl-1,3-thiazol-3-ium-2-yl)diazen-1-yl]phenyl}piperazin-1-yl)-2,5-dimethylphenyl]diazen-1-yl}-3-methyl-1,3-thiazol-3-ium

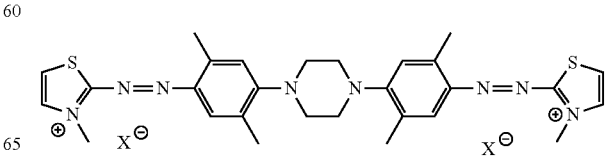

salts of 3-ethyl-2-{2-[4-(4-{4-[2-(3-ethyl-1,3-thiazol-3-ium-2-yl)diazen-1-yl]-2,5-dimethylphenyl}piperazin-1-yl)-2,5-dimethylphenyl]diazen-1-yl}-1,3-thiazol-3-ium

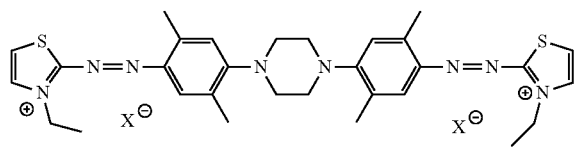

salts of 2-{2-[4-(4-{4-[2-(1,3-dimethyl-1H-imidazol-3-ium-2-yl)diazen-1-yl]phenyl}piperazin-1-yl)phenyl]diazen-1-yl}-1,3-dimethyl-1H-imidazol-3-ium

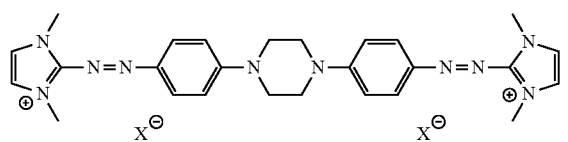

salts of 2-{2-[4-(4-{4-[2-(1,3-diethyl-1H-imidazol-3-ium-2-yl)diazen-1-yl]phenyl}piperazin-1-yl)phenyl]diazen-1-yl}-1,3-diethyl-1H-imidazol-3-ium

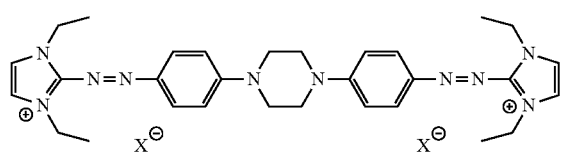

salts of 2-{2-[4-(4-{4-[2-(1,3-dimethyl-1H-imidazol-3-ium-2-yl)diazen-1-yl]-2-methylphenyl}piperazin-1-yl)-3-methylphenyl]diazen-1-yl}-1,3-dimethyl-1H-imidazol-3-ium

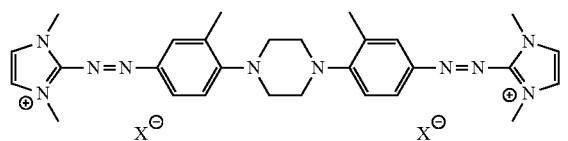

salts of 2-{2-[4-(4-{4-[2-(1,3-diethyl-1H-imidazol-3-ium-2-yl)diazen-1-yl]-2-methylphenyl}piperazin-1-yl)-3-methylphenyl]diazen-1-yl}-1,3-diethyl-1H-imidazol-3-ium

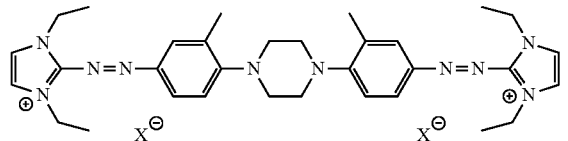

salts of 2-{2-[4-(4-{4-[2-(1,3-dimethyl-1H-imidazol-3-ium-2-yl)diazen-1-yl]-3-methylphenyl}piperazin-1-yl)-2-methylphenyl]diazen-1-yl}-1,3-dimethyl-1H-imidazol-3-ium

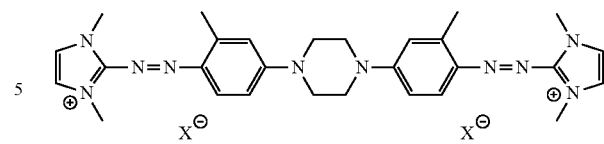

salts of 2-{2-[4-(4-{4-[2-(1,3-diethyl-1H-imidazol-3-ium-2-yl)diazen-1-yl]-3-methylphenyl}piperazin-1-yl)-2-methylphenyl]diazen-1-yl}-1,3-diethyl-1H-imidazol-3-ium

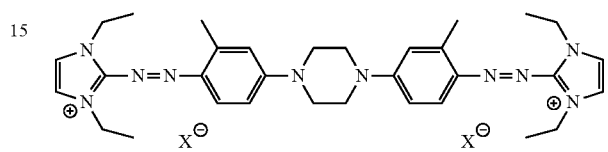

salts of 2-{2-[4-(4-{4-[2-(1,3-dimethyl-1H-imidazol-3-ium-2-yl)diazen-1-yl]-2-methoxyphenyl}piperazin-1-yl)-3-methoxyphenyl]diazen-1-yl}-1,3-dimethyl-1H-imidazol-3-ium

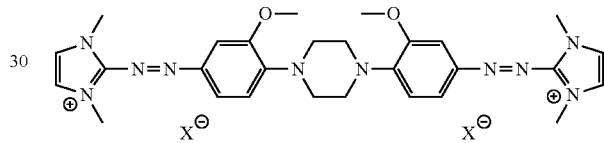

salts of 2-{2-[4-(4-{4-[2-(1,3-diethyl-1H-imidazol-3-ium-2-yl)diazen-1-yl]-2-methoxyphenyl}piperazin-1-yl)-3-methoxyphenyl]diazen-1-yl}-1,3-diethyl-1H-imidazol-3-ium

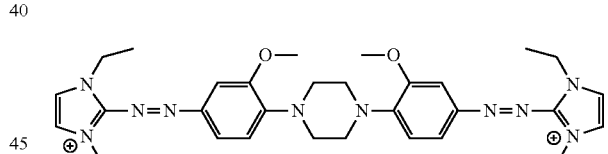

salts of 2-{2-[4-(4-{4-[2-(1,3-dimethyl-1H-imidazol-3-ium-2-yl)diazen-1-yl]-3-methoxyphenyl}piperazin-1-yl)-2-methoxyphenyl]diazen-1-yl}-1,3-dimethyl-1H-imidazol-3-ium

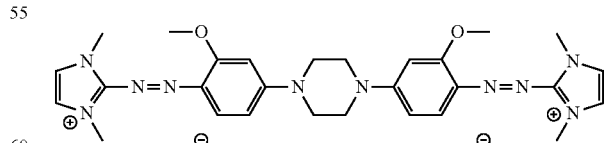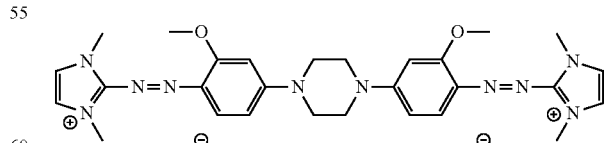

salts of 2-{2-[4-(4-{4-[2-(1,3-diethyl-1H-imidazol-3-ium-2-yl)diazen-1-yl]-3-methoxyphenyl}piperazin-1-yl)-2-methoxyphenyl]diazen-1-yl}-1,3-diethyl-1H-imidazol-3-ium

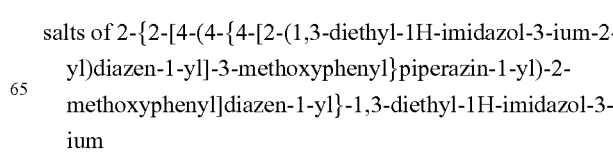

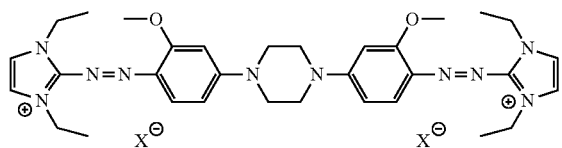

salts of 2-{2-[4-(4-{4-[2-(1,3-dimethyl-1H-imidazol-3-ium-2-yl)diazen-1-yl]-2,5-dimethylphenyl}piperazin-1-yl)-2,5-dimethylphenyl]diazen-1-yl}-1,3-dimethyl-1H-imidazol-3-ium

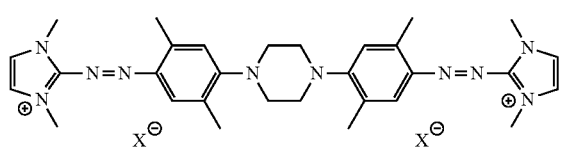

salts of 2-{2-[4-(4-{4-[2-(1,3-diethyl-1H-imidazol-3-ium-2-yl)diazen-1-yl]-2,5-dimethylphenyl}piperazin-1-yl)-2,5-dimethylphenyl]diazen-1-yl}-1,3-diethyl-1H-imidazol-3-ium

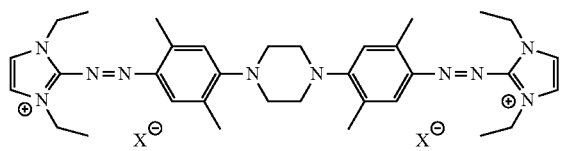

salts of 5-{2-[4-(4-{4-[2-(1,4-dimethyl-1H-1,2,4-triazol-4-ium-5-yl)diazen-1-yl]phenyl}piperazin-1-yl)phenyl]diazen-1-yl}-1,4-dimethyl-1H-1,2,4-triazol-4-ium

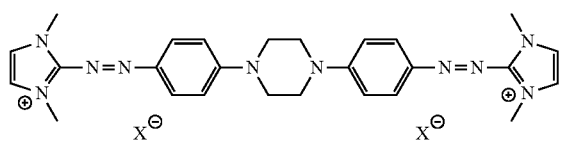

salts of 5-{2-[4-(4-{4-[2-(1,4-diethyl-1H-1,2,4-triazol-4-ium-5-yl)diazen-1-yl]phenyl}piperazin-1-yl)phenyl]diazen-1-yl}-1,4-diethyl-1H-1,2,4-triazol-4-ium

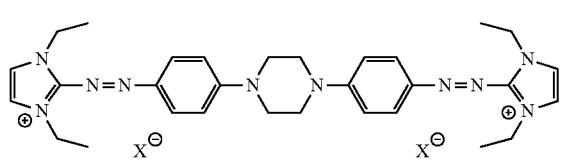

salts of 5-{2-[4-(4-{4-[2-(1,4-dimethyl-1H-1,2,4-triazol-4-ium-5-yl)diazen-1-yl]-2-methylphenyl}piperazin-1-yl)-3-methylphenyl]diazen-1-yl}-1,4-dimethyl-1H-1,2,4-triazol-4-ium

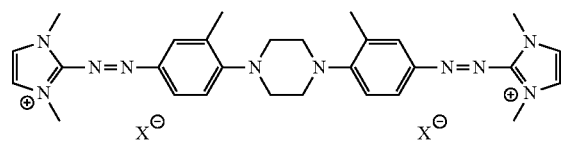

salts of 5-{2-[4-(4-{4-[2-(1,4-diethyl-1H-1,2,4-triazol-4-ium-5-yl)diazen-1-yl]-2-methylphenyl}piperazin-1-yl)-3-methylphenyl]diazen-1-yl}-1,4-diethyl-1H-1,2,4-tri-azol-4-ium

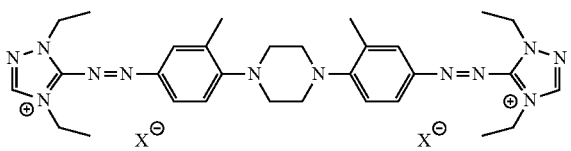

salts of 5-{2-[4-(4-{4-[2-(1,4-dimethyl-1H-1,2,4-triazol-4-ium-5-yl)diazen-1-yl]-3-methylphenyl}piperazin-1-yl)-2-methylphenyl]diazen-1-yl}-1,4-dimethyl-1H-1,2,4-tri-azol-4-ium

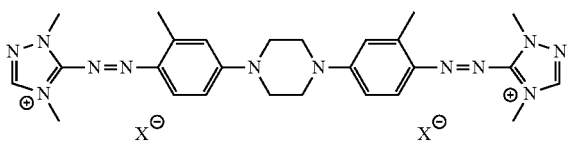

salts of 5-{2-[4-(4-{4-[2-(1,4-diethyl-1H-1,2,4-triazol-4-ium-5-yl)diazen-1-yl]-3-methylphenyl}piperazin-1-yl)-2-methylphenyl]diazen-1-yl}-1,4-diethyl-1H-1,2,4-tri-azol-4-ium

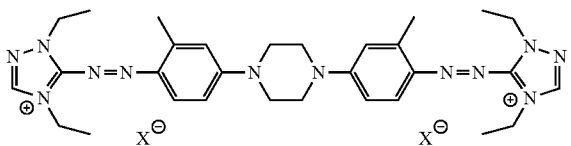

salts of 5-{2-[4-(4-{4-[2-(1,4-dimethyl-1H-1,2,4-triazol-4-ium-5-yl)diazen-1-yl]-2-methoxyphenyl}piperazin-1-yl)-3-methoxyphenyl]diazen-1-yl}-1,4-dimethyl-1H-1,2,4-triazol-4-ium

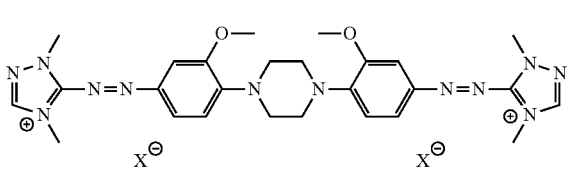

salts of 5-{2-[4-(4-{4-[2-(1,4-diethyl-1H-1,2,4-triazol-4-ium-5-yl)diazen-1-yl]-2-methoxyphenyl}piperazin-1-yl)-3-methoxyphenyl]diazen-1-yl}-1,4-diethyl-1H-1,2,4-tri-azol-4-ium

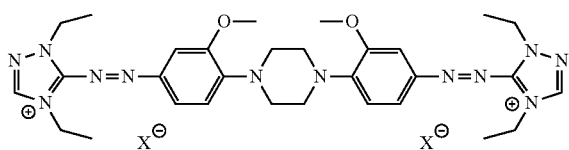

salts of 5-{2-[4-(4-{4-[2-(1,4-dimethyl-1H-1,2,4-triazol-4-ium-5-yl)diazen-1-yl]-3-methoxyphenyl}piperazin-1-yl)-2-methoxyphenyl]diazen-1-yl}-1,4-dimethyl-1H-1,2,4-triazol-4-ium

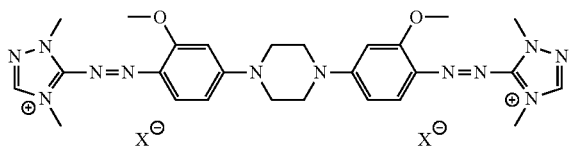

salts of 5-{2-[4-(4-{4-[2-(1,4-diethyl-1H-1,2,4-triazol-4-ium-5-yl)diazen-1-yl]-3-methoxyphenyl}piperazin-1-yl)-2-methoxyphenyl]diazen-1-yl}-1,4-diethyl-1H-1,2,4-triazol-4-ium

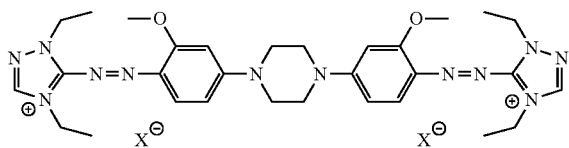

salts of 5-{2-[4-(4-{4-[2-(1,4-dimethyl-1H-1,2,4-triazol-4-ium-5-yl)diazen-1-yl]-2,5-dimethylphenyl}piperazin-1-yl)-2,5-dimethylphenyl]diazen-1-yl}-1,4-dimethyl-1H-1,2,4-triazol-4-ium

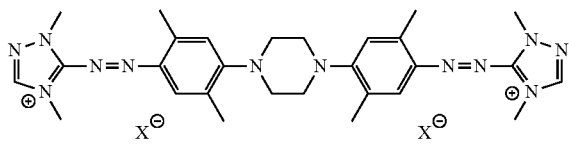

salts of 5-{2-[4-(4-{4-[2-(1,4-diethyl-1H-1,2,4-triazol-4-ium-5-yl)diazen-1-yl]-2,5-dimethylphenyl}piperazin-1-yl)-2,5-dimethylphenyl]diazen-1-yl}-1,4-diethyl-1H-1,2,4-triazol-4-ium

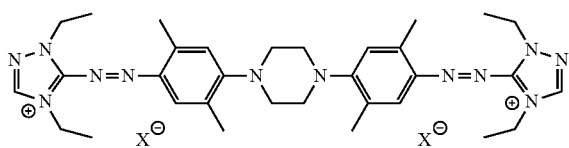

salts of 3-methyl-2-{2-[4-(5-{4-[2-(3-methyl-1,3-thiazol-3-ium-2-yl)diazen-1-yl]phenyl}-1,5-diazocan-1-yl)phenyl]diazen-1-yl}-1,3-thiazol-3-ium

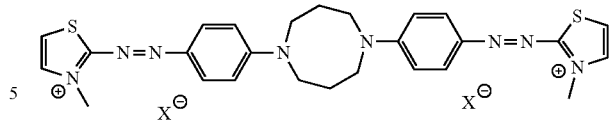

salts of 3-ethyl-2-{2-[4-(5-{4-[2-(3-ethyl-1,3-thiazol-3-ium-2-yl)diazen-1-yl]phenyl}-1,5-diazocan-1-yl)phenyl]diazen-1-yl}-1,3-thiazol-3-ium

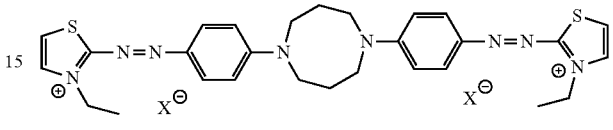

salts of 3-methyl-2-{2-[3-methyl-4-(5-{2-methyl-4-[2-(3-methyl-1,3-thiazol-3-ium-2-yl)diazen-1-yl]phenyl}-1,5-diazocan-1-yl)phenyl]diazen-1-yl}-1,3-thiazol-3-ium

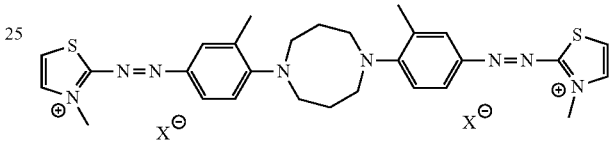

salts of 3-ethyl-2-{2-[4-(5-{4-[2-(3-ethyl-1,3-thiazol-3-ium-2-yl)diazen-1-yl]-2-methylphenyl}-1,5-diazocan-1-yl)-3-methylphenyl]diazen-1-yl}-1,3-thiazol-3-ium

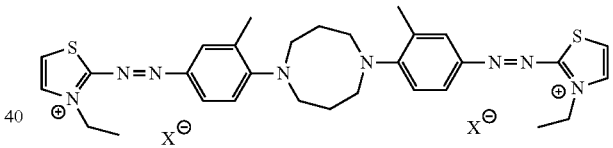

salts of 3-methyl-2-{2-[2-methyl-4-(5-{3-methyl-4-[2-(3-methyl-1,3-thiazol-3-ium-2-yl)diazen-1-yl]phenyl}-1,5-diazocan-1-yl)phenyl]diazen-1-yl}-1,3-thiazol-3-ium

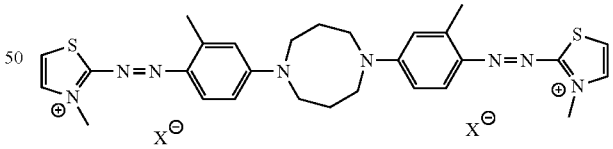

salts of 3-ethyl-2-{2-[4-(5-{4-[2-(3-ethyl-1,3-thiazol-3-ium-2-yl)diazen-1-yl]-3-methylphenyl}-1,5-diazocan-1-yl)-2-methylphenyl]diazen-1-yl}-1,3-thiazol-3-ium

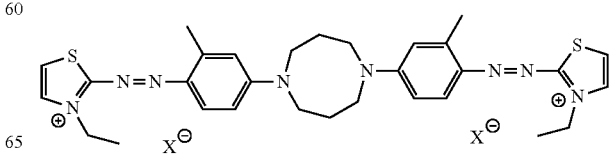

salts of 2-{2-[3-methoxy-4-(5-{2-methoxy-4-[2-(3-methyl-1,3-thiazol-3-ium-2-yl)diazen-1-yl]phenyl}-1,5-diazocan-1-yl)phenyl]diazen-1-yl}-3-methyl-1,3-thiazol-3-ium

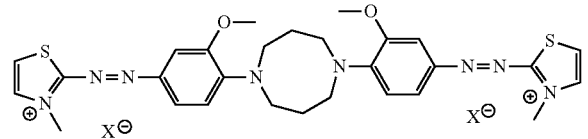

salts of 3-ethyl-2-{2-[4-(5-{4-[2-(3-ethyl-1,3-thiazol-3-ium-2-yl)diazen-1-yl]-2-methoxyphenyl}-1,5-diazocan-1-yl)-3-methoxyphenyl]diazen-1-yl}-1,3-thiazol-3-ium

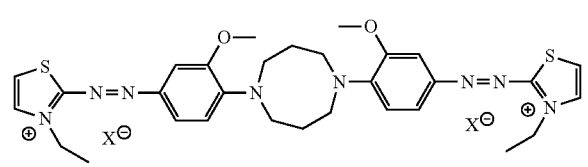

salts of 2-{2-[2-methoxy-4-(5-{3-methoxy-4-[2-(3-methyl-1,3-thiazol-3-ium-2-yl)diazen-1-yl]phenyl}-1,5-diazocan-1-yl)phenyl]diazen-1-yl}-3-methyl-1,3-thiazol-3-ium

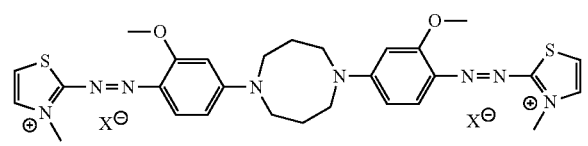

salts of 3-ethyl-2-{2-[4-(5-{4-[2-(3-ethyl-1,3-thiazol-3-ium-2-yl)diazen-1-yl]-3-methoxyphenyl}-1,5-diazocan-1-yl)-2-methoxyphenyl]diazen-1-yl}-1,3-thiazol-3-ium

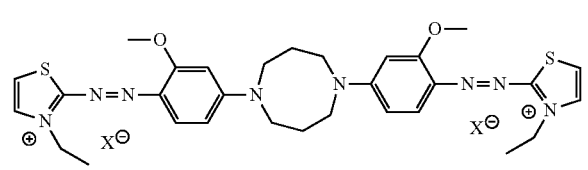

salts of 2-{2-[4-(5-{2,5-dimethyl-4-[2-(3-methyl-1,3-thiazol-3-ium-2-yl)diazen-1-yl]phenyl}-1,5-diazocan-1-yl)-2,5-dimethylphenyl]diazen-1-yl}-3-methyl-1,3-thiazol-3-ium

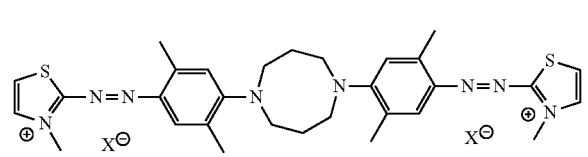

salts of 3-ethyl-2-{2-[4-(5-{4-[2-(3-ethyl-1,3-thiazol-3-ium-2-yl)diazen-1-yl]-2,5-dimethylphenyl}-1,5-diazocan-1-yl)-2,5-dimethylphenyl]diazen-1-yl}-1,3-thiazol-3-ium

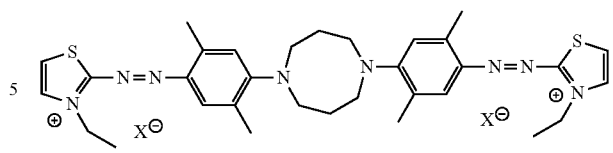

salts of 2-{2-[4-(5-{4-[2-(1,3-dimethyl-1H-imidazol-3-ium-2-yl)diazen-1-yl]phenyl}-1,5-diazocan-1-yl)phenyl]diazen-1-yl}-1,3-diethyl-1H-imidazol-3-ium

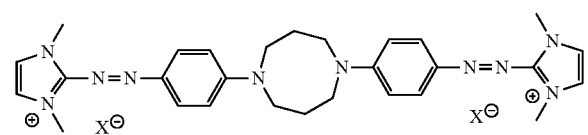

salts of 2-{2-[4-(5-{4-[2-(1,3-diethyl-1H-imidazol-3-ium-2-yl]phenyl}-1,5-diazocan-1-yl)phenyl]diazen-1-yl}-1,3-diethyl-1H-imidazol-3-ium

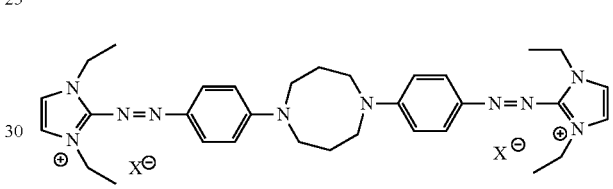

salts of 2-{2-[4-(5-{4-[2-(1,3-dimethyl-1H-imidazol-3-ium-2-yl)diazen-1-yl]-2-methylphenyl}-1,5-diazocan-1-yl)-3-methylphenyl]diazen-1-yl}-1,3-diethyl-1H-imidazol-3-ium

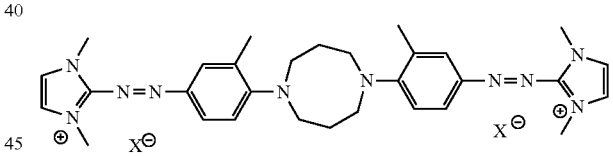

salts of 2-{2-[4-(5-{4-[2-(1,3-diethyl-1H-imidazol-3-ium-2-yl)diazen-1-yl]-2-methylphenyl}-1,5-diazocan-1-yl)-3-methylphenyl]diazen-1-yl}-1,3-diethyl-1H-imidazol-3-ium

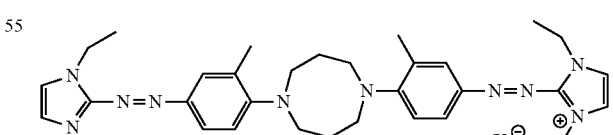

salts of 2-{2-[4-(5-{4-[2-(1,3-dimethyl-1H-imidazol-3-ium-2-yl)diazen-1-yl]-3-methylphenyl}-1,5-diazocan-1-yl)-2-methylphenyl]diazen-1-yl}-1,3-dimethyl-1H-imidazol-3-ium

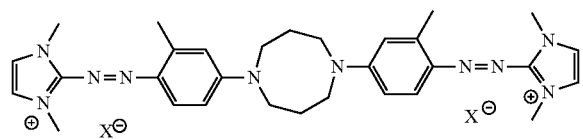

salts of 2-{2-[4-(5-{4-[2-(1,3-diethyl-1H-imidazol-3-ium-2-yl)diazen-1-yl]-3-methylphenyl}-1,5-diazocan-1-yl)-2-methylphenyl]diazen-1-yl}-1,3-diethyl-1H-imidazol-3-ium

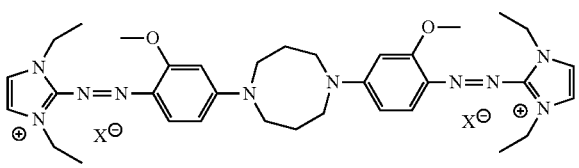

salts of 2-{2-[4-(5-{4-[2-(1,3-dimethyl-1H-imidazol-3-ium-2-yl)diazen-1-yl]-2,5-dimethylphenyl}-1,5-diazocan-1-yl)-2,5-dimethylphenyl]diazen-1-yl}-1,3-dimethyl-1H-imidazol-3-ium

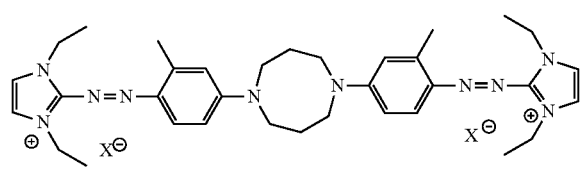

salts of 2-{2-[4-(5-{4-[2-(1,3-dimethyl-1H-imidazol-3-ium-2-yl)diazen-1-yl]-2-methoxyphenyl}-1,5-diazocan-1-yl)-3-methoxyphenyl]diazen-1-yl}-1,3-dimethyl-1H-imidazol-3-ium

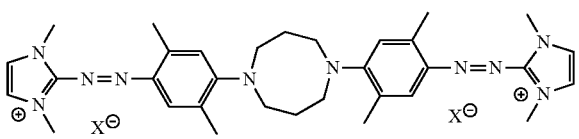

salts of 2-{2-[4-(5-{4-[2-(1,3-diethyl-1H-imidazol-3-ium-2-yl)diazen-1-yl]-2,5-dimethylphenyl}-1,5-diazocan-1-yl)-2,5-dimethylphenyl]diazen-1-yl}-1,3-diethyl-1H-imidazol-3-ium

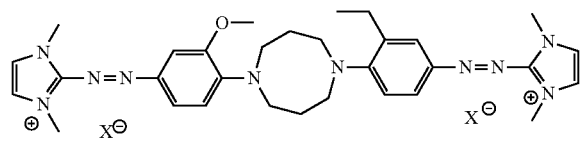

salts of 2-{2-[4-(5-{4-[2-(1,3-diethyl-1H-imidazol-3-ium-2-yl)diazen-1-yl]-2-methoxyphenyl}-1,5-diazocan-1-yl)-3-methoxyphenyl]diazen-1-yl}-1,3-diethyl-1H-imidazol-3-ium

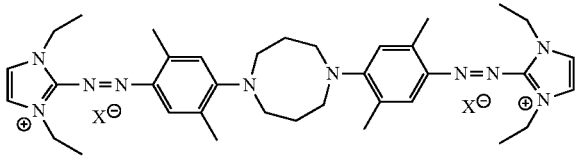

salts of 5-{2-[4-(5-{4-[2-(1,4-diethyl-1H-1,2,4-triazol-4-ium-5-yl)diazen-1-yl]phenyl}-1,5-diazocan-1-yl)phenyl]diazen-1-yl}-1,4-diethyl-1H-1,2,4-triazol-4-ium

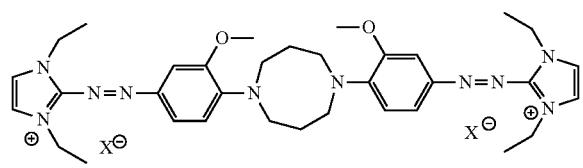

salts of 2-{2-[4-(5-{4-[2-(1,3-dimethyl-1H-imidazol-3-ium-2-yl)diazen-1-yl]-3-methoxyphenyl}-1,5-diazocan-1-yl)-2-methoxyphenyl]diazen-1-yl}-1,3-dimethyl-1H-imidazol-3-ium

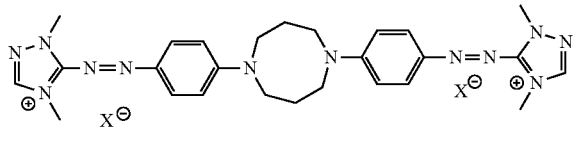

salts of 5-{2-[4-(5-{4-[2-(1,4-diethyl-1H-1,2,4-triazol-4-ium-5-yl)diazen-1-yl]phenyl}-1,5-diazocan-1-yl)phenyl]diazen-1-yl}-1,4-diethyl-1H-1,2,4-triazol-4-ium

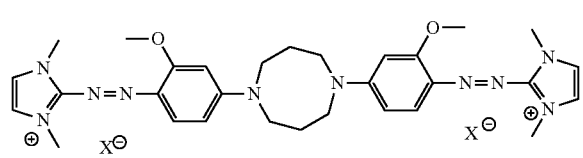

salts of 2-{2-[4-(5-{4-[2-(1,3-diethyl-1H-imidazol-3-ium-2-yl)diazen-1-yl]-3-methoxyphenyl}-1,5-diazocan-1-yl)-2-methoxyphenyl]diazen-1-yl}-1,3-diethyl-1H-imidazol-3-ium

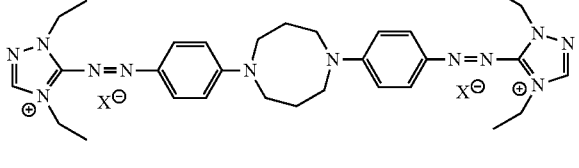

salts of 5-{2-[4-(5-{4-[2-(1,4-diethyl-1H-1,2,4-triazol-4-ium-5-yl)diazen-1-yl]-2-methylphenyl}-1,5-diazocan-1-yl)-3-methylphenyl]diazen-1-yl}-1,4-diethyl-1H-1,2,4-triazol-4-ium

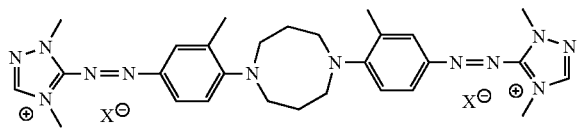

salts of 5-{2-[4-(5-{4-[2-(1,4-dimethyl-1H-1,2,4-triazol-4-ium-5-yl)diazen-1-yl]-3-methylphenyl}-1,5-diazocan-1-yl)-2-methylphenyl]diazen-1-yl}-1,4-dimethyl-1H-1,2,4-triazol-4-ium

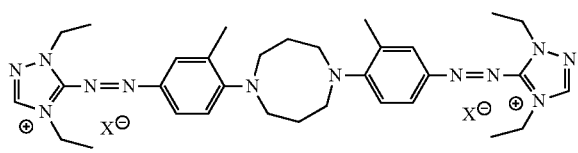

salts of 5-{2-[4-(5-{4-[2-(1,4-diethyl-1H-1,2,4-triazol-4-ium-5-yl)diazen-1-yl]-3-methylphenyl}-1,5-diazocan-1-yl)-2-methylphenyl]diazen-1-yl}-1,4-diethyl-1H-1,2,4-triazol-4-ium

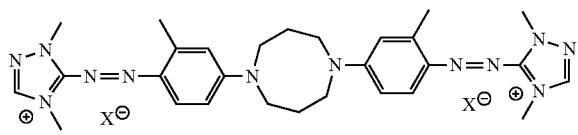

salts of 5-{2-[4-(5-{4-[2-(1,4-dimethyl-1H-1,2,4-triazol-4-ium-5-yl)diazen-1-yl]-2-methoxyphenyl}-1,5-diazocan-1-yl)-3-methoxyphenyl]diazen-1-yl}-1,4-dimethyl-1H-1,2,4-triazol-4-ium

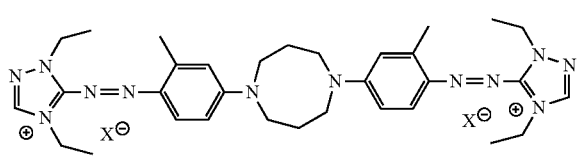

salts of 5-{2-[4-(5-{4-[2-(1,4-diethyl-1H-1,2,4-triazol-4-ium-5-yl)diazen-1-yl]-2-methoxyphenyl}-1,5-diazocan-1-yl)-3-methoxyphenyl]diazen-1-yl}-1,4-diethyl-1H-1,2,4-triazol-4-ium

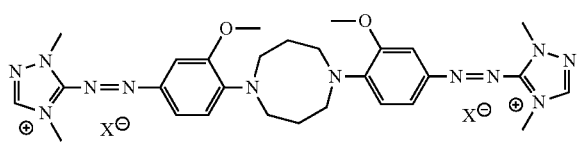

salts of 5-{2-[4-(5-{4-[2-(1,4-dimethyl-1H-1,2,4-triazol-4-ium-5-yl)diazen-1-yl]-3-methoxyphenyl}-1,5-diazocan-1-yl)-2-methoxyphenyl]diazen-1-yl}-1,4-dimethyl-1H-1,2,4-triazol-4-ium

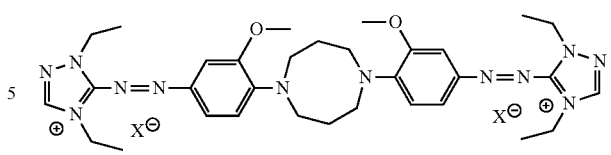

salts of 5-{2-[4-(5-{4-[2-(1,4-diethyl-1H-1,2,4-triazol-4-ium-5-yl)diazen-1-yl]-3-methoxyphenyl}-1,5-diazocan-1-yl)-2-methoxyphenyl]diazen-1-yl}-1,4-diethyl-1H-1,2,4-triazol-4-ium

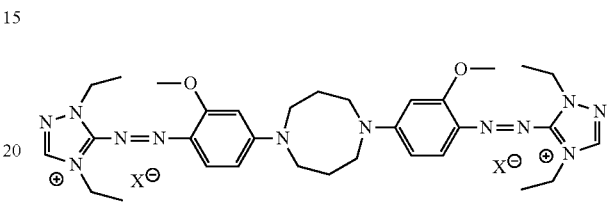

salts of 5-{2-[4-(5-{4-[2-(1,4-dimethyl-1H-1,2,4-triazol-4-ium-5-yl)diazen-1-yl]-2,5-dimethylphenyl}-1,5-diazocan-1-yl)-2,5-dimethylphenyl]diazen-1-yl}-1,4-dimethyl-1H-1,2,4-triazol-4-ium

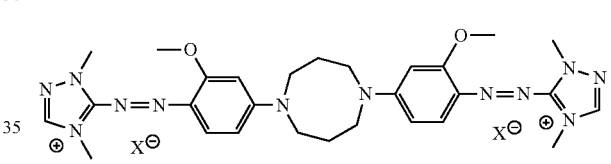

and/or
salts of 5-{2-[4-(5-{4-[2-(1,4-diethyl-1H-1,2,4-triazol-4-ium-5-yl)diazen-1-yl]-2,5-dimethylphenyl}-1,5-diazocan-1-yl)-2,5-dimethylphenyl]diazen-1-yl}-1,4-diethyl-1H-1,2,4-triazol-4-ium

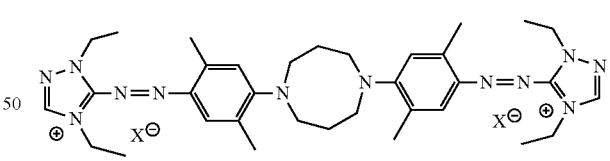

The abovementioned compounds are dicationic dimeric dyes, with the organic dication being neutralized by the two X— anions. The X— anions can each be an anion from the group of chloride, bromide, iodide, methyl sulfate, methyl sulfonate, p-toluene sulfonate, acetate, hydrogen sulfate, ½ sulfate, or ½ tetrachlorozincate.

During the work that led to this disclosure, it was found that very especially intense and oxidation-stable colorations were able to be achieved especially if direct dyes of formula (Ia) are used

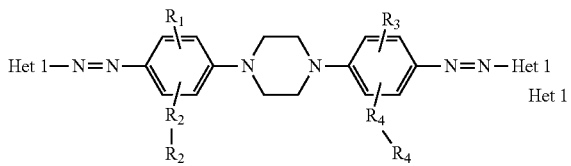
(Ia)

where
Het 1 stands for one of the structures (II), (III), or (IV),

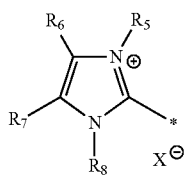
(II)

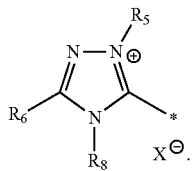
(III)

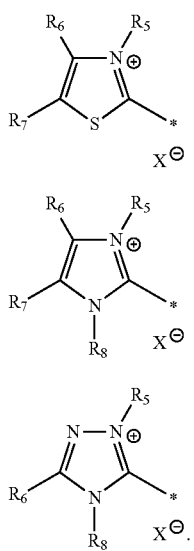
(IV)

$R^1$ stands for a hydrogen atom or for a methyl group,
$R^2$ stands for a hydrogen atom,
$R^3$ stands for a hydrogen atom or for a methyl group,
$R^4$ stands for a hydrogen atom,
$R^5$, $R^8$ independently of one another, stand for a $C_1$-$C_6$ alkyl group,
$R^6$, $R^7$ independently of one another, stand for a hydrogen atom or for a $C_1$-$C_6$ alkyl group,
X— stands in each case for a physiologically acceptable anion, preferably from the group of chloride, bromide, iodide, methyl sulfate, methyl sulfonate, p-toluene sulfonate, acetate, hydrogen sulfate, ½ sulfate, or ½ tetrachlorozincate.

Agents according to the present disclosure for dyeing keratin fibers are therefore very especially preferred which contain at least one dye (a) of formula (I) that is selected from the group of

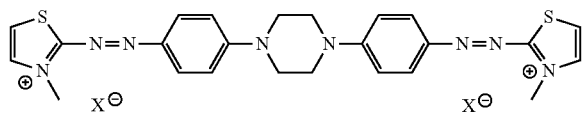

3-methyl-2-{2-[4-(4-{4-[2-(3-methyl-1,3-thiazol-3-ium-2-yl)diazen-1-yl]phenyl}piperazin-1-yl)phenyl]diazen-1-yl}-1,3-thiazol-3-ium dichloride
3-methyl-2-{2-[4-(4-{4-[2-(3-methyl-1,3-thiazol-3-ium-2-yl)diazen-1-yl]phenyl}piperazin-1-yl)phenyl]diazen-1-yl}-1,3-thiazol-3-ium dibromide
3-methyl-2-{2-[4-(4-{4-[2-(3-methyl-1,3-thiazol-3-ium-2-yl)diazen-1-yl]phenyl}piperazin-1-yl)phenyl]diazen-1-yl}-1,3-thiazol-3-ium sulfate
3-methyl-2-{2-[4-(4-{4-[2-(3-methyl-1,3-thiazol-3-ium-2-yl)diazen-1-yl]phenyl}piperazin-1-yl)phenyl]diazen-1-yl}-1,3-thiazol-3-ium di(p-toluene sulfonate)
3-methyl-2-{2-[4-(4-{4-[2-(3-methyl-1,3-thiazol-3-ium-2-yl)diazen-1-yl]phenyl}piperazin-1-yl)phenyl]diazen-1-yl}-1,3-thiazol-3-ium di(methyl sulfate)
3-methyl-2-{2-[4-(4-{4-[2-(3-methyl-1,3-thiazol-3-ium-2-yl)diazen-1-yl]phenyl}piperazin-1-yl)phenyl]diazen-1-yl}-1,3-thiazol-3-ium tetrachlorozincate

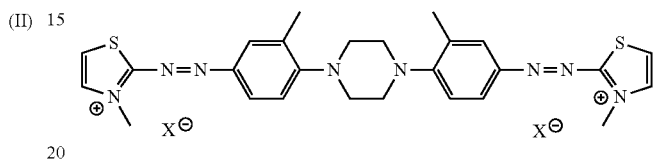

3-methyl-2-{2-[3-methyl-4-(4-{2-methyl-4-[2-(3-methyl-1,3-thiazo 1-3-ium-2-yl)diazen-1-yl]phenyl}piperazin-1-yl)phenyl]diazen-1-yl}-1,3-thiazol-3-ium dichloride
3-methyl-2-{2-[3-methyl-4-(4-{2-methyl-4-[2-(3-methyl-1,3-thiazo 1-3-ium-2-yl)diazen-1-yl]phenyl}piperazin-1-yl)phenyl]diazen-1-yl}-1,3-thiazol-3-ium dibromide
3-methyl-2-{2-[3-methyl-4-(4-{2-methyl-4-[2-(3-methyl-1,3-thiazo 1-3-ium-2-yl)diazen-1-yl]phenyl}piperazin-1-yl)phenyl]diazen-1-yl}-1,3-thiazol-3-ium sulfate
3-methyl-2-{2-[3-methyl-4-(4-{2-methyl-4-[2-(3-methyl-1,3-thiazo 1-3-ium-2-yl)diazen-1-yl]phenyl}piperazin-1-yl)phenyl]diazen-1-yl}-1,3-thiazol-3-ium di(p-toluene sulfonate)
3-methyl-2-{2-[3-methyl-4-(4-{2-methyl-4-[2-(3-methyl-1,3-thiazo 1-3-ium-2-yl)diazen-1-yl]phenyl}piperazin-1-yl)phenyl]diazen-1-yl}-1,3-thiazol-3-ium di(methyl sulfate)
3-methyl-2-{2-[3-methyl-4-(4-{2-methyl-4-[2-(3-methyl-1,3-thiazo 1-3-ium-2-yl)diazen-1-yl]phenyl}piperazin-1-yl)phenyl]diazen-1-yl}-1,3-thiazol-3-ium tetrachlorozincate

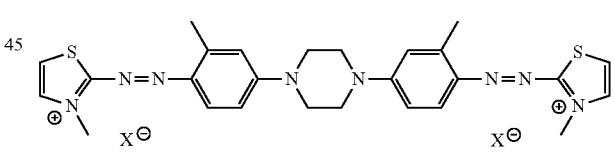

3-methyl-2-{2-[2-methyl-4-(4-{3-methy 1-4-[2-(3-methyl-1,3-thiazo 1-3-ium-2-yl)diazen-1-yl]phenyl}piperazin-1-yl)phenyl]diazen-1-yl}-1,3-thiazol-3-ium dichloride
3-methyl-2-{2-[2-methyl-4-(4-{3-methyl-4-[2-(3-methyl-1,3-thiazo 1-3-ium-2-yl)diazen-1-yl]phenyl}piperazin-1-yl)phenyl]diazen-1-yl}-1,3-thiazol-3-ium dibromide
3-methyl-2-{2-[2-methyl-4-(4-{3-methy 1-4-[2-(3-methyl-1,3-thiazo 1-3-ium-2-yl)diazen-1-yl]phenyl}piperazin-1-yl)phenyl]diazen-1-yl}-1,3-thiazol-3-ium sulfate
3-methyl-2-{2-[2-methyl-4-(4-{3-methy 1-4-[2-(3-methyl-1,3-thiazo 1-3-ium-2-yl)diazen-1-yl]phenyl}piperazin-1-yl)phenyl]diazen-1-yl}-1,3-thiazol-3-ium Di(p-toluene sulfonate)
3-methyl-2-{2-[2-methyl-4-(4-{3-methy 1-4-[2-(3-methyl-1,3-thiazo 1-3-ium-2-yl)diazen-1-yl]phenyl}piperazin-1-yl)phenyl]diazen-1-yl}-1,3-thiazol-3-ium di(methyl sulfate)

3-methyl-2-{2-[2-methyl-4-(4-{3-methyl-4-[2-(3-methyl-1,3-thiazol-3-ium-2-yl)diazen-1-yl]phenyl}piperazin-1-yl)phenyl]diazen-1-yl}-1,3-thiazol-3-ium tetrachlorozincate

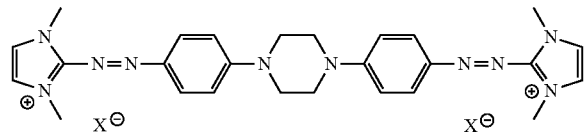

2-{2-[4-(4-{4-[2-(1,3-dimethyl-1H-imidazol-3-ium-2-yl)diazen-1-yl]phenyl}piperazin-1-yl)phenyl]diazen-1-yl}-1,3-dimethyl-1H-imidazol-3-ium dichloride 2-{2-[4-(4-{4-[2-(1,3-dimethyl-1H-imidazol-3-ium-2-yl)diazen-1-yl]phenyl}piperazin-1-yl)phenyl]diazen-1-yl}-1,3-dimethyl-1H-imidazol-3-ium dibromide 2-{2-[4-(4-{4-[2-(1,3-dimethyl-1H-imidazol-3-ium-2-yl)diazen-1-yl]phenyl}piperazin-1-yl)phenyl]diazen-1-yl}-1,3-dimethyl-1H-imidazol-3-ium sulfate 2-{2-[4-(4-{4-[2-(1,3-dimethyl-1H-imidazol-3-ium-2-yl)diazen-1-yl]phenyl}piperazin-1-yl)phenyl]diazen-1-yl}-1,3-dimethyl-1H-imidazol-3-ium di(p-toluene sulfonate)

2-{2-[4-(4-{4-[2-(1,3-dimethyl-1H-imidazol-3-ium-2-yl)diazen-1-yl]phenyl}piperazin-1-yl)phenyl]diazen-1-yl}-1,3-dimethyl-1H-imidazol-3-ium di(methyl sulfate)

2-{2-[4-(4-{4-[2-(1,3-dimethyl-1H-imidazol-3-ium-2-yl)diazen-1-yl]phenyl}piperazin-1-yl)phenyl]diazen-1-yl}-1,3-dimethyl-1H-imidazol-3-ium tetrachlorozincate

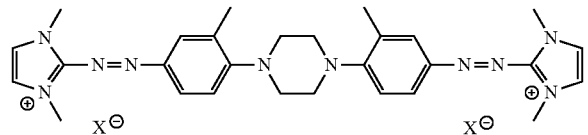

2-{2-[4-(4-{4-[2-(1,3-dimethyl-1H-imidazol-3-ium-2-yl)diazen-1-yl]-2-methylphenyl}piperazin-1-yl)-3-methylphenyl]diazen-1-yl}-1,3-dimethyl-1H-imidazol-3-ium dichloride 2-{2-[4-(4-{4-[2-(1,3-dimethyl-1H-imidazol-3-ium-2-yl)diazen-1-yl]-2-methylphenyl}piperazin-1-yl)-3-methylphenyl]diazen-1-yl}-1,3-dimethyl-1H-imidazol-3-ium dibromide 2-{2-[4-(4-{4-[2-(1,3-dimethyl-1H-imidazol-3-ium-2-yl)diazen-1-yl]-2-methylphenyl}piperazin-1-yl)-3-methylphenyl]diazen-1-yl}-1,3-dimethyl-1H-imidazol-3-ium sulfate 2-{2-[4-(4-{4-[2-(1,3-dimethyl-1H-imidazol-3-ium-2-yl)diazen-1-yl]-2-methylphenyl}piperazin-1-yl)-3-methylphenyl]diazen-1-yl}-1,3-dimethyl-1H-imidazol-3-ium di(p-toluene sulfonate)

2-{2-[4-(4-{4-[2-(1,3-dimethyl-1H-imidazol-3-ium-2-yl)diazen-1-yl]-2-methylphenyl}piperazin-1-yl)-3-methylphenyl]diazen-1-yl}-1,3-dimethyl-1H-imidazol-3-ium Di(methyl sulfate)

2-{2-[4-(4-{4-[2-(1,3-dimethyl-1H-imidazol-3-ium-2-yl)diazen-1-yl]-2-methylphenyl}piperazin-1-yl)-3-methylphenyl]diazen-1-yl}-1,3-dimethyl-1H-imidazol-3-ium tetrachlorozincate

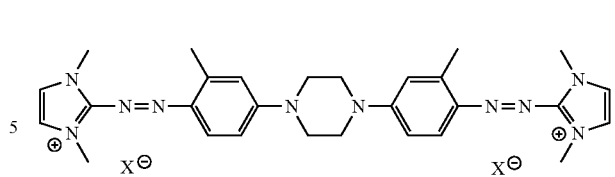

2-{2-[4-(4-{4-[2-(1,3-dimethyl-1H-imidazol-3-ium-2-yl)diazen-1-yl]-3-methylphenyl}piperazin-1-yl)-2-methylphenyl]diazen-1-yl}-1,3-dimethyl-1H-imidazol-3-ium dichloride 2-{2-[4-(4-{4-[2-(1,3-dimethyl-1H-imidazol-3-ium-2-yl)diazen-1-yl]-3-methylphenyl}piperazin-1-yl)-2-methylphenyl]diazen-1-yl}-1,3-dimethyl-1H-imidazol-3-ium dibromide 2-{2-[4-(4-{4-[2-(1,3-dimethyl-1H-imidazol-3-ium-2-yl)diazen-1-yl]-3-methylphenyl}piperazin-1-yl)-2-methylphenyl]diazen-1-yl}-1,3-dimethyl-1H-imidazol-3-ium sulfate 2-{2-[4-(4-{4-[2-(1,3-dimethyl-1H-imidazol-3-ium-2-yl)diazen-1-yl]-3-methylphenyl}piperazin-1-yl)-2-methylphenyl]diazen-1-yl}-1,3-dimethyl-1H-imidazol-3-ium di(p-toluene sulfonate)

2-{2-[4-(4-{4-[2-(1,3-dimethyl-1H-imidazol-3-ium-2-yl)diazen-1-yl]-3-methylphenyl}piperazin-1-yl)-2-methylphenyl]diazen-1-yl}-1,3-dimethyl-1H-imidazol-3-ium Di(methyl sulfate)

2-{2-[4-(4-{4-[2-(1,3-dimethyl-1H-imidazol-3-ium-2-yl)diazen-1-yl]-3-methylphenyl}piperazin-1-yl)-2-methylphenyl]diazen-1-yl}-1,3-dimethyl-1H-imidazol-3-ium tetrachlorozincate

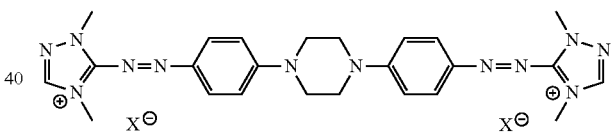

5-{2-[4-(4-{4-[2-(1,4-dimethyl-1H-1,2,4-triazol-4-ium-5-yl)diazen-1-yl]phenyl}piperazin-1-yl)phenyl]diazen-1-yl}-1,4-dimethyl-1H-1,2,4-triazol-4-ium dichloride 5-{2-[4-(4-{4-[2-(1,4-dimethyl-1H-1,2,4-triazol-4-ium-5-yl)diazen-1-yl]phenyl}piperazin-1-yl)phenyl]diazen-1-yl}-1,4-dimethyl-1H-1,2,4-triazol-4-ium dibromide 5-{2-[4-(4-{4-[2-(1,4-dimethyl-1H-1,2,4-triazol-4-ium-5-yl)diazen-1-yl]phenyl}piperazin-1-yl)phenyl]diazen-1-yl}-1,4-dimethyl-1H-1,2,4-triazol-4-ium sulfate 5-{2-[4-(4-{4-[2-(1,4-dimethyl-1H-1,2,4-triazol-4-ium-5-yl)diazen-1-yl]phenyl}piperazin-1-yl)phenyl]diazen-1-yl}-1,4-dimethyl-1H-1,2,4-triazol-4-ium di(p-toluene sulfonate)

5-{2-[4-(4-{4-[2-(1,4-dimethyl-1H-1,2,4-triazol-4-ium-5-yl)diazen-1-yl]phenyl}piperazin-1-yl)phenyl]diazen-1-yl}-1,4-dimethyl-1H-1,2,4-triazol-4-ium di(methyl sulfate)

5-{2-[4-(4-{4-[2-(1,4-dimethyl-1H-1,2,4-triazol-4-ium-5-yl)diazen-1-yl]phenyl}piperazin-1-yl)phenyl]diazen-1-yl}-1,4-dimethyl-1H-1,2,4-triazol-4-ium tetrachlorozincate

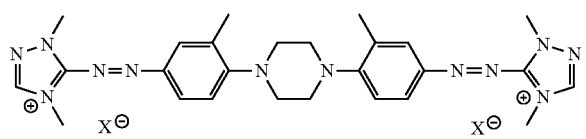

5-{2-[4-(4-{4-[2-(1,4-dimethyl-1H-1,2,4-triazol-4-ium-5-yl)diazen-1-yl]-2-methylphenyl}piperazin-1-yl)-3-methylphenyl]diazen-1-yl}-1,4-dimethyl-1H-1,2,4-triazol-4-ium dichloride 5-{2-[4-(4-{4-[2-(1,4-dimethyl-1H-1,2,4-triazol-4-ium-5-yl)diazen-1-yl]-2-methylphenyl}piperazin-1-yl)-3-methylphenyl]diazen-1-yl}-1,4-dimethyl-1H-1,2,4-triazol-4-ium dibromide 5-{2-[4-(4-{4-[2-(1,4-dimethyl-1H-1,2,4-triazol-4-ium-5-yl)diazen-1-yl]-2-methylphenyl}piperazin-1-yl)-3-methylphenyl]diazen-1-yl}-1,4-dimethyl-1H-1,2,4-triazol-4-ium sulfate 5-{2-[4-(4-{4-[2-(1,4-dimethyl-1H-1,2,4-triazol-4-ium-5-yl)diazen-1-yl]-2-methylphenyl}piperazin-1-yl)-3-methylphenyl]diazen-1-yl}-1,4-dimethyl-1H-1,2,4-triazol-4-ium di(p-toluene sulfonate)

5-{2-[4-(4-{4-[2-(1,4-dimethyl-1H-1,2,4-triazol-4-ium-5-yl)diazen-1-yl]-2-methylphenyl}piperazin-1-yl)-3-methylphenyl]diazen-1-yl}-1,4-dimethyl-1H-1,2,4-triazol-4-ium di(methyl sulfate)

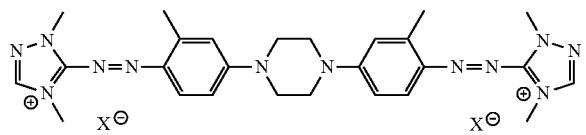

5-{2-[4-(4-{4-[2-(1,4-dimethyl-1H-1,2,4-triazol-4-ium-5-yl)diazen-1-yl]-3-methylphenyl}piperazin-1-yl)-2-methylphenyl]diazen-1-yl}-1,4-dimethyl-1H-1,2,4-triazol-4-ium dichloride 5-{2-[4-(4-{4-[2-(1,4-dimethyl-1H-1,2,4-triazol-4-ium-5-yl)diazen-1-yl]-3-methylphenyl}piperazin-1-yl)-2-methylphenyl]diazen-1-yl}-1,4-dimethyl-1H-1,2,4-triazol-4-ium dibromide 5-{2-[4-(4-{4-[2-(1,4-dimethyl-1H-1,2,4-triazol-4-ium-5-yl)diazen-1-yl]-3-methylphenyl}piperazin-1-yl)-2-methylphenyl]diazen-1-yl}-1,4-dimethyl-1H-1,2,4-triazol-4-ium sulfate 5-{2-[4-(4-{4-[2-(1,4-dimethyl-1H-1,2,4-triazol-4-ium-5-yl)diazen-1-yl]-3-methylphenyl}piperazin-1-yl)-2-methylphenyl]diazen-1-yl}-1,4-dimethyl-1H-1,2,4-triazol-4-ium di(p-toluene sulfonate)

5-{2-[4-(4-{4-[2-(1,4-dimethyl-1H-1,2,4-triazol-4-ium-5-yl)diazen-1-yl]-3-methylphenyl}piperazin-1-yl)-2-methylphenyl]diazen-1-yl}-1,4-dimethyl-1H-1,2,4-triazol-4-ium di(methyl sulfate)

5-{2-[4-(4-{4-[2-(1,4-dimethyl-1H-1,2,4-triazol-4-ium-5-yl)diazen-1-yl]-3-methylphenyl}piperazin-1-yl)-2-methylphenyl]diazen-1-yl}-1,4-dimethyl-1H-1,2,4-triazol-4-ium tetrachlorozincate The agents according to the present disclosure for dyeing keratin fibers preferably contain the direct dye(s) or formula (I) in a total quantity from about 0.01 to about 4.5 wt %, preferably from about 0.05 to about 2.8 wt %, more preferably from about 0.1 to about 2.2 wt %, and especially preferably from about 0.2 to about 1.2 wt %. The indicated quantity in weight percent refers here to the total quantity of all of the compounds of formula (I) contained in the agent in relation to the total weight of the agent.

In another preferred embodiment, an agent according to the present disclosure for dyeing keratin fibers is therefore characterized in that it contains—with respect to the total weight of the agent—one or more direct dyes (a) of formula (I) in a total quantity from about 0.01 to about 4.5 wt %, preferably about 0.05 to about 2.8 wt %, more preferably about 0.1 to about 2.2 wt %, and especially preferably about 0.2 to about 1.2 wt %.

The dyes of general formula (I) can be manufactured using a method analogous to the method described in WO 2002/100369 A2.

For instance, the reactant 2-aminothiazol can be converted in concentrated sulfuric acid with nitrosylsulfuric acid into the diazonium ion:

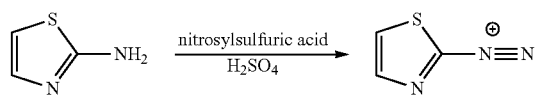 [SMILES: Nc1nccs1 ; "H2SO4" ; N#[N+]c1nccs1]

The reactive diazonium ion then undergoes a double azo coupling reaction with the dimeric aniline derivatives.

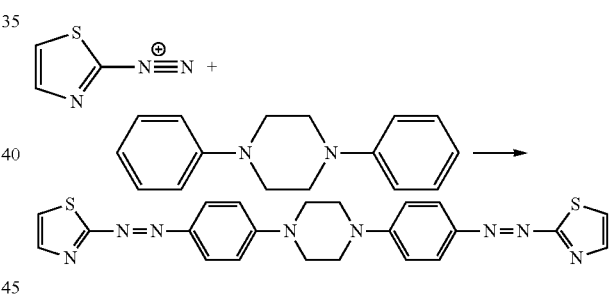

The reactant 2-diphenyl piperazine, which can be used in the azo coupling reaction, can be manufactured according to one of the following synthesis paths, for example:

Journal of Heterocyclic Chemistry, 14, p. 535, 1977
The Journal of Organic Chemistry, 52, p. 1673, 1987
Tetrahedron Letters, 27, p. 377, 1986.

The neutral dimeric dye produced in the azo coupling reaction can then finally be double-quaternized with quaternizing agents. The quaternization reaction is preferably carried out in a polar aprotic solvent (such as DMSO, DMF, etc.). Some examples of quaternizing agents that are worthy of consideration are diethyl sulfate, methyl bromide, or p-toluene sulfonate.

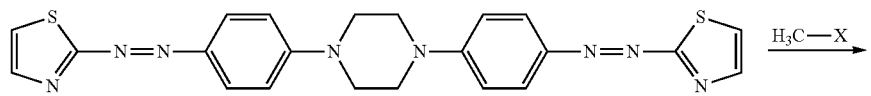

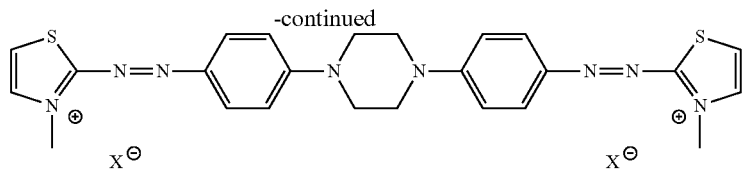

Another method for manufacturing these dyes is disclosed in GB1186753, for example.

In an especially preferred embodiment, the agents according to the present disclosure additionally contain at least one surfactant. It was found in this regard that very intense coloration results were able to be obtained particularly if the agents according to the present disclosure additionally contained at least one anionic surfactant (b).

Surfactants are amphiphilic (bifunctional) compounds that consists of at least one hydrophobic and at least one hydrophilic moiety. The hydrophobic residue is preferable a hydrocarbon chain with 8-24 carbon atoms that can be saturated or unsaturated, linear or branched. Especially preferably, this $C_8$-$C_{24}$ alkyl chain is linear.

In anionic surfactants, the hydrophilic moiety comprises a negatively charged hydrophilic headgroup. For example, the negatively charged hydrophilic headgroup can be a carboxylic acid group or the salt of a carboxylic acid group, a sulfonic acid group or the salt of a sulfonic acid group, a sulfuric acid ester grouping or salt thereof, a phosphonic acid group or the salt of the phosphonic acid group, or a phosphonic acid ester grouping or salt thereof.

The cosmetic agent according to the present disclosure usually comprises an aqueous carrier. In aqueous solution, the abovementioned hydrophilic headgroups of the anionic surfactant—such as the carboxylic acid and the salts of the carboxylic acids, for example—are present in an equilibrium, the condition of which is partially determined by the pH value of the agent. Therefore, if a fatty acid is used as an anionic surfactant, for example, a small portion of the fatty acid is present in aqueous solution in the form of the protonated fatty acid, whereas the majority of the fatty acid is deprotonated in aqueous solution and thus converted into the salt of the fatty acid. For this reason, the definition of an anionic surfactant also includes surfactants with an acid group that is still protonated.

An anionic surfactant (b) in terms of the present disclosure does not contain any cationic groupings—that is, zwitterionic surfactants are not included by the definition of an anionic surfactant.

Anionic surfactants according to the present disclosure are therefore characterized by the presence of a water-solubilizing, anionic group such as a carboxylate, sulfate, sulfonate or phosphate group and a lipophilic alkyl group with about 8 to 30 C atoms. In addition, glycol or polyglycol ether groups, ester, ether and amide groups as well as hydroxyl groups can be contained in the molecule. Typical examples of anionic surfactants are alkylbenzene sulfonates, alkane sulfonates, olefin sulfonates, alkyl ether sulfonates, glycerin ether sulfonates, a-methyl ester sulfonates, sulfo fatty acids, alkyl sulfates, fatty alcohol ether sulfates, glycerin ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl tartrates, acyl glutamates, acyl aspartates, alkyl oligoglucoside sulfates, protein fatty acid condensates (particularly wheat-based plant products), and alkyl (ether) phosphates. Insofar as the anionic surfactants contain polyglycol ether chains, these can have a conventional—but preferably a narrowed—homolog distribution.

Examples of anionic surfactants according to the present disclosure are, each in the form of the sodium, potassium, and ammonium salts as well as the mono-, di-, and trialkanol ammonium salts with 2 to 4 carbon atoms in the alkanol group, linear and branched fatty acids with 8 to 30 C-atoms (soaps), ether carboxylic acids of the formula R—O—($CH_2$—$CH_2O$)$_x$—$CH_2$—COOH, in which R is a linear alkyl group with 8 to 30 C-atoms and x=0 or 1 to 16, acyl sarcosides with 8 to 24 C-atoms in the acyl group, acyl taurides with 8 to 24 C-atoms in the acyl group, acyl isethionates with 8 to 24 C-atoms in the acyl group, which can be obtained through esterification of fatty acids with the sodium salt of 2-hydroxyethane sulfonic acid (isethionic acid). If fatty acids with 8 to 24 C atoms—e.g., lauric, myristic, palmitic, or stearic acid or also technical fatty acid fractions, such as the $C_{12}$-$C_{18}$ fatty acid fraction that can be obtained from coconut fatty acid—are used for this esterification, the $C_{12}$-$C_{18}$ acyl isethionates that are preferably suitable according to the present disclosure are obtained, sulfosuccinic acid mono- and dialkyl esters with 8 to 24 C-atoms in the alkyl group and sulfosuccinic acid mono-alkylpolyoxyethyl esters with 8 to 24 C-atoms in the alkyl group and 1 to 6 oxyethyl groups. Sulfosuccinic acid mono- and dialkyl esters can be produced by converting maleic anhydride with a fatty alcohol with 8 to 24 C atoms to form the maleic acid monoester of the fatty alcohol, and subsequent reaction with sodium sulfite to form the sulfosuccinic acid ester. Especially suitable sulfosuccinic acid esters are derived from fatty alcohol fractions with 12 to 18 C atoms, such as those which can be obtained from coconut fatty acid or coconut fatty acid methyl ester through hydration, linear alkane sulfonate sulfonates with 8 to 24 C-atoms, linear alpha-olefin sulfonates with 8 to 24 C atoms, alpha-sulfo fatty acid methyl esters of fatty acids with 8 to 30 C atoms, alkyl sulfates and alkyl polyglycol ether sulfates of the formula R—O($CH_2$—$CH_2O$)$_x$—$OSO_3H$, in which R is a preferably linear alkyl group with 8 to 30 C-atoms and x=0 or 1 to 12, hydroxy sulfonates corresponding substantially to at least one of the two following formulas or mixtures and salts thereof, $CH_3$—$(CH_2)_y$—CHOH—$(CH_2)$p-(CH—$SO_3M$)-$(CH_2)_z$—$CH_2$—O—$(CnH2nO)_x$—H, and/or $CH_3$—$(CH_2)_y$—(CH—$SO_3M$)-$(CH_2)_p$—CHOH—$(CH_2)_z$—$CH_2$—O—$(CnH2nO)_x$—H, where, in both formulas, y and z=0 or integers from 1 to 18, p=0, 1, or 2, and the sum (y+z+p) is a number from 12 to 18, x=0 or a number from 1 to 30 and n is an integer from 2 to 4 and M=H or alkali, particularly sodium, potassium, lithium, alkaline earth, particularly magnesium, calcium, zinc and/or an ammonium ion, which can be optionally substituted, particularly mono-, di-, tri-, or tetraammonium ions with $C_1$ to $C_4$ alkyl, Alkenyl, or aryl residues, sulfated hydroxyalkyl polyethylene and/or hydroxyalkylene propylene glycol ethers of the formula RL $(CHOSO_3M)$-$CHR^3$—$(OCHR^4$—$CH_2)_n$—$OR^2$, where $R^1$ stands for a linear alkyl residue with 1 to 24 C atoms, $R^2$ stands for a linear or branched, saturated alkyl residue with 1 to 24 C atoms, $R^3$ stands for hydrogen or a linear alkyl residue with 1 to 24 C atoms, $R^4$ stands for hydrogen or a methyl residue, and M stands for hydrogen, ammonium, alkyl ammonium, alkanol ammonium, with the alkyl and alkanol residues each having 1 to 4 C atoms, or a metal ion selected from among lithium, sodium, potassium, calcium, or magnesium, and n stands for a number in the range from 0 to 12, and the total number of C atoms contained in $R^1$ and $R^3$ is still 2 to 44, sulfonates of unsaturated fatty acids with 8 to 24 C atoms and 1 to 6 double bonds, esters of tartaric acid and citric acid with alcohols, which represent addition products of about 2-15 molecules of ethylene oxide and/or propylene oxide on fatty alcohols with 8 to 22 C atoms, alkyl and/or alkenyl ether phosphates of the formula $R^1(OCH_2CH_2)_n$—O—(PO—OX)—$OR^2$, in which $R^1$ preferably stands for an aliphatic hydrocarbon residue with 8 to 30 carbon atoms, $R^2$ stands for hydrogen, a $(CH_2CH_2O)_nR^2$ residue or X, n stands for numbers from 1 to 10, and X stands for hydrogen, an alkali or earth alkaline metal or $NR^3R^4R^5R^6$, where $R^3$ to $R^6$, independently of one another, stand for hydrogen or a $C_1$ to $C_4$ hydrocarbon residue, sulfated fatty acid alkylene glycol esters of the formula $RCO(AlkO)_nSO_3M$ in which RCO— stands for a linear or branched, aliphatic, saturated and/or unsaturated acyl residue with 6 to 22 C atom, Alk stands for $CH_2CH_2$, $CHCH_3CH_2$ and/or $CH_2CHCH_3$, n stands for numbers from 0.5 to 5, and M stands for a metal, such as an alkali metal, particularly sodium, potassium, lithium, alkaline earth metal, particularly magnesium, calcium, zinc, or ammonium ion, such as $+NR^3 R^4 R^5 R^6$, where $R^3$ to $R^6$, independently of one another, stand for hydrogen or a $C_1$ to $C_4$ hydrocarbon residue, monoglyceride sulfates and monoglyceride ether sulfates of the formula $R^8OC$—$(OCH_2CH_2)_x$—$OCH_2$—$[CHO(CH_2CH_2O)_yH]$—$CH_2O(CH_2CH_2O)_z$—$SO_3X$, in which $R^8CO$ stands for a linear or branched acyl residue with 6 to 22 carbon atoms, x, y, and z in sum stand for 0 or for numbers from 1 to 30, preferably 2 to 10, and X stands for an alkali or alkaline earth metal. Typical examples for monoglyceride (ether) sulfates that are suitable in terms of the present disclosure are the conversion products of lauric acid monoglyceride, coconut fatty acid monoglyceride, palmitic acid monoglyceride, stearic acid monoglyceride, oleic acid monoglyceride, and tallow fatty acid monoglyceride, as well as the ethylene oxide adducts thereof with sulfur trioxide or chlorosulfonic acid in the form of their sodium salts. Monoglyceride sulfates are preferably used in which $R^8CO$ stands for an acyl residue with 8 to 18 carbon atoms, amide ether carboxylic acids, $RLCO$—$NR^2$—$CH_2CH_2$—O—$(CH_2CH_2O)_n CH_2COOM$, where $R^1$ is a straight-chain or branched alkyl or alkenyl residue with a number of carbon atoms in the chain from 2 to 30, n stands for an integer from 1 to 20 and $R^2$ stands for hydrogen, a methyl, ethyl, propyl, isopropyl, n-butyl, t-butyl-, or iso-butyl residue, and M stands for hydrogen or a metal such as alkali metal, particularly sodium, potassium, lithium, alkaline earth metal, particularly magnesium, calcium, zinc, or an ammonium ion, such as $+NR^3 R^4 R^5 R^6$, where $R^3$ to $R^6$, independently of one another, stand for hydrogen or a $C_1$ to $C_4$ hydrocarbon residue. Such products are available from Chem-Y under the product name Akypo®, for example, and acyl glutamates of the formula XOOC—$CH_2CH_2CH(C(NH)OR)$—COOX, in which RCO stands for a linear or branched acyl residue with 6 to 22 carbon atoms and 0 and/or 1, 2, or 3 double bonds and X stands for hydrogen, an alkali and/or alkaline earth metal, ammonium, alkyl ammonium, alkanol ammonium, or glucammonium.

The treatment of keratin fibers with agents containing (a) at least one direct dye of formula (I) and (b) at least one anionic surfactant resulted in especially intense colorations in attractive nuances. Surprisingly, it was found that the color-lifting capability was able to be optimized even further through the use of one or more special anionic surfactants. Especially intense blue colorations were obtained if the dyes (a) of formula (I) were used which had at least one anionic surfactant (b) from the group of the linear and branched fatty acids with 8 to 30 C atoms, ether carboxylic acids of the formula R—O—$(CH_2$—$CH_2O)_x$—$CH_2$—COOH, in which R is a linear alkyl group with 8 to 30 C-atoms and x=0 or 1 to 16, acyl sarcosides with 8 to 24 C-atoms in the acyl group, acyl taurides with 8 to 24 C-atoms in the acyl group, acyl isethionates with 8 to 24 C-atoms in the acyl group, which can be obtained through esterification of fatty acids with the sodium salt of 2-hydroxyethane sulfonic acid (isethionic acid). If fatty acids with 8 to 24 C atoms—e.g., lauric, myristic, palmitic, or stearic acid or also technical fatty acid fractions, such as the $C_{12}$-$C_{18}$ fatty acid fraction that can be obtained from coconut fatty acid—are used for this esterification, the $C_{12}$-$C_{18}$ acyl isethionates that are preferably suitable according to the present disclosure are obtained, amide ether carboxylic acids, $RLCO$—$NR^2$—$CH_2CH_2$—O—$(CH_2CH_2O)_nCH_2COOM$, where $R^1$ is a straight-chain or branched alkyl or alkenyl residue with a number of carbon atoms in the chain from 2 to 30, n stands for an integer from 1 to 20 and $R^2$ stands for hydrogen, a methyl, ethyl, propyl, isopropyl, n-butyl, t-butyl-, or iso-butyl residue, and M stands for hydrogen or a metal such as alkali metal, particularly sodium, potassium, lithium, alkaline earth metal, particularly magnesium, calcium, zinc, or an ammonium ion, such as $+NR^3 R^4 R^5 R^6$, where $R^3$ to $R^6$, independently of one another, stand for hydrogen or a $C_1$ to $C_4$ hydrocarbon residue. Such products are available from Chem-Y under the product name Akypo®, for example, and acyl glutamates of the formula XOOC—$CH_2CH_2CH(C(NH)OR)$—COOX, in which RCO stands for a linear or branched acyl residue with 6 to 22 carbon atoms and 0 and/or 1, 2, or 3 double bonds and X stands for hydrogen, an alkali and/or alkaline earth metal, ammonium, alkyl ammonium, alkanol ammonium, or glucammonium.

In another especially preferred embodiment, an agent according to the present disclosure is therefore characterized in that it (b) contains at least one anionic surfactant that is selected from the linear and branched fatty acids with 8 to 30 C atoms, ether carboxylic acids of the formula R—O—($CH_2$—$CH_2$O)$_x$—$CH_2$—COOM, in which
R stands for a linear alkyl group with 8 to 30 C atoms,
x stands for an integer from 0 to 16,
M stands for hydrogen or a metal such as an alkali metal, particularly sodium, potassium, lithium, an alkaline earth metal, particularly ½ magnesium, ½ calcium, ½ zinc, or an ammonium ion ($NH_4^+$),
  acyl sarcosides with 8 to 24 C-atoms in the acyl group,
  acyl taurides with 8 to 24 C-atoms in the acyl group,
  acyl isethionates with 8 to 24 C atoms in the acyl group, which can be obtained through the esterification of $C_8$-$C_{24}$ fatty acids with the sodium salt of 2-hydroxyethane sulfonic acid (isethionic acid), amide ether carboxylic acids, $R^1$—CO—NR 2-$CH_2CH_2$—O—($CH_2CH_2O$)$_y$$CH_2$COOM, where
$R^1$ stands for a $C_2$-$C_{30}$ alkyl group,
y stands for an integer from 1 to 20,
$R^2$ stands for hydrogen, methyl, ethyl, propyl, isopropyl, n-butyl, t-butyl, or iso-butyl residue, and
M stands for hydrogen or a metal such as an alkali metal, particularly sodium, potassium, lithium, an alkaline earth metal, particularly ½ magnesium, ½ calcium, ½ zinc, or an ammonium ion ($NH_4$).

An especially good color-lifting capability was observed when at least one ether carboxylic acid of the formula R—O—($CH_2$—$CH_2O$)$_x$—$CH_2$—COOH or salt thereof was used as an anionic surfactant (b). The use of—optionally ethoxylated—ether carboxylic acids is therefore explicitly very especially preferred.

In an explicitly very especially preferred embodiment, an agent according to the present disclosure is therefore characterized in that it contains at least one anionic surfactant (b) from the group of the ether carboxylic acids of formula (B1)

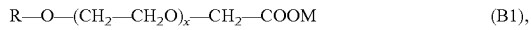

where
R stands for a linear alkyl group with 8 to 30 C atoms,
x stands for an integer from 0 to 16,
M stands for hydrogen or a metal such as an alkali metal, particularly sodium, potassium, lithium, an alkaline earth metal, particularly ½ magnesium, ½ calcium, ½ zinc, or an ammonium ion ($NH_4^+$). Also especially preferably, x stands for the numbers 5, 6, or 7.

In another very especially preferred embodiment, an agent according to the present disclosure is therefore characterized in that it contains at least one ether carboxylic acid of formula (B1) as an anionic surfactant (b)

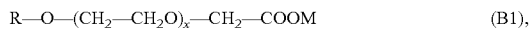

where
R stands for a linear alkyl group with 8 to 30 C atoms,
x stands for an integer from 5 to 11, particularly for the numbers 5, 6, or 7,
M stands for hydrogen or a metal such as an alkali metal, particularly sodium, potassium, lithium, an alkaline earth metal, particularly ½ magnesium, ½ calcium, ½ zinc, or an ammonium ion ($NH_4^+$).

The very especially preferred anionic surfactants of formula (B1) are available, for example, under the trade name
  Akypo Soft 45 HP from Kao (sodium laureth-6 carboxylate)
  Akypo Soft 45 NV from Kao (sodium laureth-5 carboxylate)
  Akypo RLM 100 NV from Kao (sodium laureth-11 carboxylate)

Preferably, the agents according to the present disclosure for dyeing keratin fibers contain one or more surfactants (b) in a total quantity from about 0.05 to about 4.5 wt %, preferably from about 0.1 to about 2.1 wt %, more preferably from about 0.15 to about 1.8 wt %, and very especially preferably from about 0.2 to about 0.9 wt %. The indicated quantities in wt % refer here to the total quantity of all anionic surfactants (b) in relation to the total quantity of the dye.

In another especially preferred embodiment, an agent according to the present disclosure for dyeing keratin fibers is therefore characterized in that it contains—with respect to the total weight of the agent—one or more anionic surfactants (b) in a total quantity from about 0.05 to about 9.5 wt %, preferably about 0.1 to about 3.1 wt %, more preferably about 0.15 to about 2.5 wt %, and especially preferably about 0.2 to about 0.9 wt %.

As described previously, it was found that, by varying the anionic surfactant(s) (b), the color-lifting capability of the direct dyes of formula (I) can be influenced.

In general, color lifting can be improved through the use of at least one anionic surfactant. The use of at least one—optionally ethoxylated—ether carboxylic acid and/or salt thereof, as is described in formula (B1), has proven to be especially advantageous in this context. It was observed that the keratin fibers were able to be dyed in especially intense nuances when the ether carboxylic acid(s) (and/or salts thereof) were contained in the agent according to the present disclosure as the main anionic surfactant.

In other words, the coloring results were especially intense when the agents according to the present disclosure contained one or more ether carboxylic acids of formula (B1) and when, in addition, all other anionic surfactants used were present only in small quantities. The use of the ether carboxylic acid(s) of formula (B1) as the main surfactant can be quantified by indicating a weight ratio of the total quantity of the anionic surfactants of formula (B1) contained in the agent to the total quantity of all anionic surfactants (b) contained in the agent.

In another especially preferred embodiment, an agent according to the present disclosure for dyeing keratin fibers is therefore characterized in that the weight ratio of all of the anionic surfactants of formula (B1) contained in the agent to the total quantity of the anionic surfactants contained in the agent is about 0.5, preferably about 0.6, more preferably about 0.75, and especially preferably about 0.9,
with the anionic surfactants of formula (B1) being the following surfactants R—O—($CH_2$—$CH_2O$)$_x$—$CH_2$—COOM (B1),
where
R is equal to a linear alkyl group with 8 to 30 C atoms,
x is equal to an integer from 0 to 16,
M is equal to hydrogen or a metal such as an alkali metal, particularly sodium, potassium, lithium, an alkaline earth metal, particularly ½ magnesium, ½ calcium, ½ zinc, or an ammonium ion ($NH_4^+$).

Example: An agent for dyeing keratin fibers contains:
(a) 1.0 g 3-methyl-2-{2-[4-(4-{4-[2-(3-methyl-1,3-thiazol-3-ium-2-yl)diazen-1-yl]phenyl}piperazin-1-yl)phenyl]diazen-1-yl}-1,3-thiazol-3-ium di(methylsulfate)
(b) 0.23 g sodium laureth-6 carboxylate (B1), and
(c) 0.10 g sodium laureth sulfate (2 EO)

The weight ratio of all of the anionic surfactants of formula (B1) contained in the agent to the total quantity of the anionic surfactants contained in the agent is [0.23/(0.23+0.1)]=0.70.

Example: An agent for dyeing keratin fibers contains:
(a) 0.5 g 3-methyl-2-{2-[4-(4-{4-[2-(3-methyl-1,3-thiazol-3-ium-2-yl)diazen-1-yl]phenyl}piperazin-1-yl)phenyl]diazen-1-yl}-1,3-thiazol-3-ium di(methylsulfate)
(b) 0.23 g sodium laureth-6 carboxylate (B1) and no other anionic surfactants The weight ratio of all of the anionic surfactants of formula (B1) contained in the agent to the total quantity of the anionic surfactants contained in the agent is [0.23/0.23]=1.0.

Moreover, the agents according to the present disclosure can also contain one or more cationic surfactants. Cationic surfactants are understood as being surfactants, i.e., surface-active compounds, that each have one or more positive charges. Cationic surfactants contain exclusively positive charges. Usually, these surfactants are constructed from a hydrophobic part and a hydrophilic headgroup, with the hydrophobic part generally consisting of a hydrocarbon framework (e.g., consisting of one or two linear or branched alkyl chains), and with the positive charge(s) being located in the hydrophilic headgroup. Cationic surfactants adsorb on boundary surfaces and aggregate in aqueous solution above the critical micelle concentration.

Examples of cationic surfactants are
quaternary ammonium compounds that can bear one or two alkyl chains with a chain length of 8 to 28 C atoms as hydrophobic residues
quaternary phosphonium salts, substituted with one or more alkyl chains with a chain length of 8 to 28 C atoms, or
tertiary sulfonium salts.

Moreover, the cationic charge can also be a component of a heterocyclic ring (e.g., of an imidazolium ring or pyridinium ring) in the form of an onium structure.

Besides the functional moiety that bears the cationic charge, the cationic surfactant can also contain other uncharged functional groups, which is the case with esterquats, for example. Some examples of suitable cationic surfactants of this type are physiologically acceptable salts of N,N,N-trimethyl-1-hexadecanaminium, particularly N,N,N-trimethyl-1-hexadecanaminium, which is also sold under the trade name Dehyquart A-CA.

Another suitable cationic surfactant is a physiologically acceptable salt of dimethyl distearyl dimethyl ammonium, especially preferably dimethyl distearyl ammonium chloride.

Additional cationic surfactants can be selected from the group of the cationic imidazolium compounds.

The agent according to the present disclosure can contain the cationic surfactants in a total quantity of about 0.1 to about 4.8 wt %, preferably about 0.2 to about 2.4 wt %, more preferably about 0.3 to about 1.8 with respect to the total weight of agent.

Moreover, it has proven advantageous if the agents contain other, non-ionogenic boundary surface-active substances. Preferred nonionic surfactants are alkyl polyglycosides as well as alkylene oxide addition products to fatty alcohols, and fatty acids, each with 2 to 30 mols of ethylene oxide per mol of fatty alcohol or fatty acid. Preparations with outstanding characteristics are also obtained if they contain fatty acid esters of ethoxylated glycerin as nonionic surfactants.

The nonionic surfactants are used in proportions of about 1.0 to about 45 wt %, preferably about 1 to about 30 wt %, and very especially preferably about 1 to about 15 wt % with respect to the total quantity of the ready-to-use agent.

In another preferred embodiment, the agents according to the present disclosure, in addition to the compound of formula (I), also contain at least one other direct dye. Through the combination with other cationic direct dyes, the achievable nuance spectrum can be expanded and the dyeing characteristics improved even further.

Direct dyes can be categorized into anionic, cationic and nonionic direct dyes.

The direct dyes additionally contained in the agent are preferably selected from among the cationic direct dyes, since they have good compatibility with the dyes of formula (I).

In another especially preferred embodiment, an agent according to the present disclosure is therefore characterized in that it at least additionally contains least one additional direct dye that is different from the dyes of formula (I).

One or more dyes from the group of Basic Yellow 87, Basic Orange 31, Basic Red 51, Basic Violet 2, and Cationic Blue 347 have proven to have especially good compatibility.

The dyes of formula (I) with the cationic azo dyes Basic Orange 31 and Basic Red 51 have very especially good compatibility. By combining a dye of formula (I) with Basic Orange 31 and/or Basic Red 51, nuances over the entire color spectrum can be produced with the exception of the pure yellow nuances.

In another especially preferred embodiment, an agent according to the present disclosure is characterized in that it additionally contains Basic Orange 31 and/or Basic Red 51.

However, the agent according to the present disclosure can also additionally contain at least one nonionic direct dye. This can be selected from the group of HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 3,4-ethylamino-3-nitrobenzoic acid, and 2-chloro-6-ethylamino-4-nitrophenol.

In addition, anionic direct dyes can also be contained which are known by the international designations and/or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol Blue, and Tetrabromophenol Blue. Furthermore, the agents according to the present disclosure can also be used together with oxidation dyeing agents. Such oxidation dyeing agents additionally contain at least one oxidation dye precursor, preferably at least one oxidation dye precursor of the developer type and at least one oxidation dye precursor of the coupler type. Especially suitable oxidation dye precursors of the developer type are selected from at least one compound from the group consisting of p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-Amino-3-methylphenyl)-N-[3-(1H-imidazole-1-yl)propyl]amine, N,N'-bis-(2-hydroxyethyl)-N,N'-bis-(4-aminophenyl)-1,3-diaminopropane2-ol, bis-(-2-hydroxy-5-aminophenyl)methane, 1,3-Bis-(2,5-diaminophenoxy)-propane-2-ol, N,N'-bis-(4-aminophenyl)-1,4-diazacycloheptane, 1-bis-(2,5-diaminophenyl)-1,4,7-tetraoxadecane, 4-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazol, 2,4,5,6-tetraaminopyrimidine, 4-hydroxy-2,5,6-triaminopyrimidine, 2-hydroxy-4,5,6-triaminopyrimidine, and the physiologically acceptable salts thereof.

Especially suitable oxidation dye precursors of the coupler type are selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-Bis(2'-hydroxyethylamino)-1-methylbenzene, 2-{3-[(2-hydroxyethyl)amino]-4-methoxy-5-methylphenyl}amino)ethanol, 2-{3-[(2-hydroxyethyl)amino]-2-methoxy-5-methylphenyl}amino)ethanol, 2-{3-[(2-hydroxyethyl)amino]-4,5-dimethylphenyl}amino)ethanol, 2-[3-morpholine-4-ylphenyl)amino]ethanol, 3-amino-4-(2-methoxyethoxy)-5-methylphenylamine, 1-amino-3-bis-(2-hydroxyethyl)aminobenzene, resorcin, 2-methylresorcin, 4-chlororesorcin, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-on, 1-naphthol, 1,5-dihydroxynaphthalene, 2,7-dihydroxynaphthalene, 1,7-dihydroxynaphthalene, 1,8-dihydroxynaphthalene, 4-hydroxyindol, 6-hydroxyindol, 7-hydroxyindol, 4-hydroxyindoline, 6-hydroxyindoline and/or 7-hydroxyindoline, or mixtures of these compounds or physiologically acceptable salts thereof.

The additional direct dyes, developer components, and coupler components are preferably each used in a proportion of about 0.0001 to about 5.0 wt %, preferably about 0.001 to about 3.5 wt %, each with respect to the ready-to-use agent. Developer components and coupler components are generally used in approximate molar quantities in relation to each other. Although molar use has proven to be expedient, a certain excess of individual oxidation dye precursors is not disadvantageous, so that developer components and coupler components can be present in a molar ratio of about 1:0.5 to 1:3, particularly about 1:1 to 1:2.

If the dyeing with the direct dyes according to the present disclosure of formula (I) and the oxidative lightening of the keratin fibers are to be performed in one step, then the agents according to the present disclosure additionally contain an oxidizing agent, preferably hydrogen peroxide and/or one of the solid addition products thereof to organic or inorganic compounds.

In a preferred embodiment, hydrogen peroxide itself is used as an aqueous solution. The concentration of a hydrogen peroxide solution in the agent according to the present disclosure is determined by the legal requirements on the one hand and by the desired effect on the other hand; preferably, about 6 to about 12 wt % solutions in water are used. Ready-to-use agents of the first object of the present disclosure that are preferred according to the present disclosure are characterized in that they contain, with respect to the total weight of the ready-to-use agent, about 0.5 to about 20 wt %, preferably about 1 to about 12.5 wt %, especially preferably about 2.5 to about 10 wt %, and particularly about 3 to about 6 wt % hydrogen peroxide, each with respect to the total weight of the agent.

In another especially preferred embodiment, an agent according to the present disclosure is characterized in that it contains, with respect to the total weight of the agent, about 0.5 to about 12.5 wt %, preferably about 2.5 to about 10 wt %, and particularly about 3 to about 6 wt % hydrogen peroxide.

To achieve an intensified lightening and bleaching effect, the agent can also contain at least one peroxo salt. Suitable peroxo salts are inorganic peroxo compounds, preferably selected from the group consisting of ammonium peroxodisulfate, alkali metal peroxodisulfates, ammonium peroxomonosulfate, alkali metal peroxomonosulfates, alkali metal peroxodiphosphates, and alkaline earth metal peroxides. Peroxodisulfates, particularly ammonium peroxodisulfate, potassium peroxodisulfate, and sodium peroxodisulfate, are especially preferred.

In another especially preferred embodiment, an agent according to the present disclosure is characterized in that it additionally contains at least one persulfate from the group of ammonium peroxodisulfate, potassium peroxodisulfate, and sodium peroxodisulfate.

The persulfates are each contained in the agent according to the present disclosure in a quantity of about 0.5 to about 20 wt %, preferably about 1 to about 12.5 wt %, especially preferably about 2.5 to about 10 wt %, and particularly about 3 to about 6 wt % with respect to the total weight of the ready-to-use agent.

Ammonium peroxodisulfate is a compound of the formula $(NH_4)_2S_2O_8$. Potassium peroxodisulfate is a compound of the formula $K_2S_2O_8$. Sodium peroxodisulfate is a compound of the formula $Na_2S_2O_8$.

In another especially preferred embodiment, an agent according to the present disclosure is characterized in that it contains—with respect to the total weight of the agent—one or more persulfates from the group of ammonium peroxodisulfate, potassium peroxodisulfate, and sodium peroxodisulfate in a total quantity from about 0.5 to about 20 wt %, preferably about 1.0 to about 12.5 wt %, more preferably about 2.5 to about 10 wt %, and especially preferably about 3.0 to about 6.0 wt %.

In another especially preferred embodiment, an agent according to the present disclosure is characterized in that it contains—with respect to the total weight of the agent—(c) one or more persulfates from the group of ammonium peroxodisulfate, potassium peroxodisulfate, and sodium peroxodisulfate in a total quantity from about 0.5 to about 20 wt %, preferably about 1.0 to about 12.5 wt %, more preferably about 2.5 to about 10 wt %, and especially preferably about 3.0 to about 6.0 wt %.

The direct dyes according to the present disclosure of general formula (I) have proven to be especially stable in relation to certain mixtures of ammonium peroxodisulfate, potassium peroxodisulfate, and sodium peroxodisulfate.

In another especially preferred embodiment, an agent according to the present disclosure is characterized in that it contains, with respect to the total weight of the agent, about 0.2 to about 13.5 wt %, preferably about 0.5 to about 1.5 wt % ammonium peroxodisulfate about 0.5 to about 4.5 wt %, preferably about 1.5 to about 2.5 wt % potassium peroxodisulfate, and about 0.2 to about 1.8 wt %, preferably about 0.4 to about 0.8 wt % sodium peroxodisulfate.

The dyeing and/or matting agent can contain additional bleach boosters in order to intensify the blonding effect, such as tetraacetylethylethylenediamine (TAED), 1,5-diacetyl-2,4-dioxo-hexahydro-1,3,5-triazine (DADHT), tetraacetyl glycoluril (TAGU), N-nonanoyl succinimide (NOSI), n-nonanoyl or isononanoyl oxybenzene sulfonate (n- and i-NOBS, respectively), phthalic acid anhydride, triacetin, ethylene glycol diacetate, and 2,5-diacetoxy-2,5-dihydrofuran, as well as carbonate salts and hydrogen carbonate salts, particularly ammonium hydrogen carbonate, ammonium carbonate, sodium hydrogen carbonate, disodium carbonate, potassium hydrogen carbonate, dipotassium carbonate, and calcium carbonate, and nitrogen-containing, heterocyclic bleach boosters, such as 4-acetyl-1-methyl pyridinium-p-toluene sulfonate, 2-acetyl-1-methyl pyridinium-p-toluene sulfonate, as well as N-methyl-3,4-dihydroisoquinolinium-p-toluene sulfonate.

To further increase the lightening effect, at least one $SiO_2$ compound, such as silicic acid or silicates, particularly water glasses, can be additionally added to the composition according to the present disclosure. It may be preferred according to the present disclosure to use the $SiO_2$ compounds in quantities from about 0.05 wt % to about 15 wt %, especially preferably in quantities from about 0.15 wt % to about 10 wt %, and very especially preferably in quantities from about 0.2 wt % to about 5 wt %, each with respect to the water-free composition according to the present disclosure. The indicated quantities represent the content of the $SiO_2$ compounds (without their water component) in the agents.

The colorants can also contain additional active substances, adjuvants, and additives in order to improve the coloring performance and set additional desired characteristics of the agents.

Preferably, the colorants are prepared as a liquid preparation and another, surface-active substance is therefore optionally added to the agents, with such surface-active substances being referred to as surfactants or as emulsifiers, depending on the area of application: They are preferably selected from among anionic, zwitterionic, amphoteric and nonionic surfactants and emulsifiers.

The colorants according to the present disclosure can contain additional adjuvants and additives. For instance, it has proven to be advantageous if the agent contains at least one thickener. In principle, no restrictions exist with respect to these thickeners. Both organic and purely inorganic thickeners can be used.

Suitable thickeners are
anionic, synthetic polymers;
cationic, synthetic polymers;
naturally occurring thickeners such as nonionic guar gums, scleroglucan gums, or xanthan gums, gum arabic, ghatti gum, karaya gum, tragacanth gum, carrageenan gum, agar-agar, locust bean gum, pectins, alginates, starch fractions and derivatives such as amylose, amylopectin, and dextrins, as well as cellulose derivatives, such as methyl cellulose, carboxyalkyl celluloses, and hydroxyalkyl celluloses;
nonionic, fully synthetic polymers, such as polyvinyl alcohol or polyvinyl pyrrolidone; as well as
inorganic thickeners, particularly layered silicates such as bentonite, for example, especially smectites such as montmorillonite or hectorite.

Dyeing processes on keratin fibers usually take place in an alkaline medium. In order to protect the keratin fibers and the skin to the greatest possible extent, however, the pH value should not be set too high. It is therefore preferred if the pH value of the ready-to-use agent is between about 7 and about 11, particularly between about 8 and about 10.5. The pH values in terms of the present disclosure are pH values that are measured at a temperature of about 22° C.

The alkalizing agents that can be used according to the present disclosure for setting the preferred pH value can be selected from the group consisting of ammoniac, alkanolamines, basic amino acids, as well as inorganic alkalizing agents such as alkaline (earth) metal hydroxides, alkaline (earth) metal silicates, alkaline (earth) metal phosphates, and alkaline (earth) metal hydrogen phosphates. Preferred inorganic alkalizing agents are magnesium carbonate, sodium hydroxide, potassium hydroxide, sodium silicate, and sodium metasilicate. Organic alkalizing agents that can be used according to the present disclosure are preferably selected from among monoethanolamine, 2-amino-2-methylpropanol and triethanolamine. The basic amino acids that can be used as an alkalizing agent according to the present disclosure are preferably selected from the group consisting of arginine, lysine, omithine and histidine, especially preferably arginine. However, it was found in the context of the investigations leading to the present disclosure that agents that are preferred according to the present disclosure are further characterized in that they additionally contain an organic alkalizing agent. One embodiment of the first object of the present disclosure is characterized in that the agent additionally contains at least one alkalizing agent that is selected from the group consisting of ammoniac, alkanolamines, and basic amino acids, particularly ammoniac, monoethanolamine, and arginine or acceptable salts thereof.

Furthermore, it has proven advantageous if the colorants, particularly if they additionally contain hydrogen peroxide, contain at least one stabilizer or complexing agent. Especially preferred stabilizers are phenacetin, alkali benzoates (sodium benzoate), and salicylic acid. Moreover, all complexing agents of the prior art can be used. Complexing agents that are preferred according to the present disclosure are nitrogen-containing polycarboxylic acids, particularly EDTA and EDDS, and phosphonates, particularly 1-hydroxyethane-1,1-diphosphonate (HEDP) and/or ethylenediamine tetramethylene phosphonate (EDTMP) and/or diethylene triamine pentamethylene phosphonate (DTPMP) or sodium salts thereof.

Furthermore, the agents according to the present disclosure can contain additional active substances, adjuvants and additives, such as, for example, nonionic polymers such as, for example, vinylpyrrolidone/vinyl acrylate copolymers, polyvinylpyrrolidone, vinylpyrrolidone/vinyl acetate copolymers, polyethylene glycols and polysiloxanes; additional silicones such as volatile or nonvolatile, straight-chain, branched or cyclic, crosslinked or non-crosslinked polyalkylsiloxanes (such as dimethicone or cyclomethicone), polyarylsiloxanes and/or polyalkylarylsiloxanes, particularly polysiloxane with organofunctional groups, such as substituted or unsubstituted amines (amodimethicone), carboxyl, Alkoxy and/or hydroxyl groups (dimethicone copolyols), linear polysiloxane(A)-polyoxyalkylene(B) block copolymers, grafted silicon polymers; cationic polymers such as quaternized cellulose ethers, polysiloxanes with quaternary groups, dimethyldiallyl ammonium chloride polymers, acrylamide dimethyldiallyl ammonium chloride copolymers, dimethylamino-ethylmethacrylate vinylpyrrolidone copolymers quaternized with diethyl sulfate, vinylpyrrolidone imidazolinium methochloride copolymers and quaternized polyvinyl alcohol; zwitterionic and amphoteric polymers; anionic polymers such as, for example, polyacrylic acids or crosslinked polyacrylic acids; structurants such as glucose, maleic acid and lactic acid, hair-conditioning compounds such as phospholipids, for example lecithin and cephaline; perfume oils, dimethyl isosorbide and cyclodextrins; fiber structure-improving active substances, particularly mono-, di- and oligosaccharides such as, for example, glucose, galactose, fructose, fruit sugar and lactose; colorants for coloring the agent; anti-dandruff agents such as piroctone olamine, zinc omadine and climbazol; amino acids and oligopeptides; animal- and/or plant-based protein hydrolysates, as well as in the form of their fatty acid condensation products or, optionally, anionically or cationically modified derivatives; plant oils; light stabilizers and UV blockers; active substances such as panthenol, pantothenic acid, pantolactone, allantoin, pyrrolidone carboxylic acids and salts thereof, as well as bisabolol; polyphenoles, particularly hydroxycinnamic acids, 6,7-dihydroxycoumarins, hydroxybenzoic acids, catechins, tannins, leucoanthocyanidins, anthocyanidins, flavanones, flavones and flavonols; ceramides or pseudo-ceramides; vitamins, provitamins and vitamin precursors; plant extracts; fats and waxes such as fatty alcohols, beeswax, montan wax and paraffins; swelling and penetration agents such as glycerin, propylene glycol monoethyl ethers, carbonates, hydrogen carbonates, guanidine, ureas as well as primary, secondary and tertiary phosphates; opacifiers such as latex, styrene/PVP and styrene/acrylamide copolymers; pearlescent agents such as ethylene glycol mono- and distearate as well as PEG-3 distearate; pigments, as well as propellants such as propane/butane mixtures, N2O, dimethyl ether, CO2 and air.

The selection of these other substances is made by a person skilled in the art depending on the desired characteristics of the agents. As regards other optional components as well as the quantities of these components used, express reference is made to the relevant handbooks known to a person skilled in the art. The additional active substances and adjuvants are preferably each used in the agents according to the present disclosure in quantities from about 0.0001 to about 25 wt %, particularly from about 0.0005 to about 15 wt %, with respect to the total weight of the mixture for application.

The agents of the first object of the present disclosure can be used in methods for dyeing and in methods for the simultaneous blonding or lightening and dyeing of human hair.

The agents according to the present disclosure can be formulated and applied appropriately as single-component agents or as multiple-component agents such as two-component agents or three-component agents. The separation into multiple-component systems is particularly expedient if incompatibilities of the ingredients are expected or feared; in such systems, the agent to be used is prepared by the consumer immediately before application by mixing the components.

The agent according to the present disclosure for dyeing keratin fibers is always understood as the ready-to-use agent.

If the agent according to the present disclosure is made available to the user in the form of a single-component agent, then the ready-to-use agent need not be first prepared, but rather it can be removed right away from the container in which it was packaged and applied to the keratin fibers.

However, bleaching agents are usually two-component products in which an oxidizing agent-containing component (A1) is mixed shortly before application with an (alkalizing) agent (A2), and this ready-to-use mixture is applied to the hair.

In this case, the agent according to the present disclosure is the ready-to-use agent that was prepared shortly before application through the mixing of (A1) and (A2).

The direct dyes of general formula (I) can be packaged in component (A1) (i.e., together with the oxidizing agent) or in component (A2) (together with the alkalizing agent).

It is also possible and in keeping with the present disclosure if the ready-to-use agent is prepared shortly before being applied to the human hair through the mixing of 3 components, in which case
- the component (A1) contains at least one direct dye of general formula (I) and at least one alkalizing agent,
- the component (A2) contains at least one oxidizing agent (e.g., hydrogen peroxide), and
- the component (A3) contains at least a second oxidizing agent (e.g., one or more peroxydisulfate salts).

During the exposure time of the agents on the fiber, it can be advantageous to support the lightening process or the mattifying process by supplying heat. The heat supply can be provided by means of an external heat source, such as warm air from a hot-air blower, and—particularly when the hair of a living test subject is being lightened—through the test subject's body heat. In the case of the latter possibility, the area being treated is usually covered by a hood. An exposure phase at room temperature is also in keeping with the present disclosure. In particular, if the temperature during the exposure time lies between about 20° C. and about 40° C., particularly between about 25° C. and about 38° C. After the exposure time, the remaining dyeing preparation is rinsed out of the hair with water or a cleaning agent. Commercially available shampoo in particular can act as a cleaning agent, in which case the cleaning agent can be omitted and the rinsing process can be performed using water if, in particular, the lightening agent has a high surfactant content.

As regards other preferred embodiments of the use and method according to the present disclosure, the remarks concerning the agents according to the present disclosure apply mutatis mutandis.

EXAMPLES

Direct Dye 1: 3-methyl-2-{2-[4-(4-{4-[2-(3-methyl-1,3-thiazol-3-ium-2-yl)diazen-1-yl]phenyl}piperazin-1-yl)phenyl]diazen-1-yl}-1,3-thiazol-3-ium dimethyl sulfate

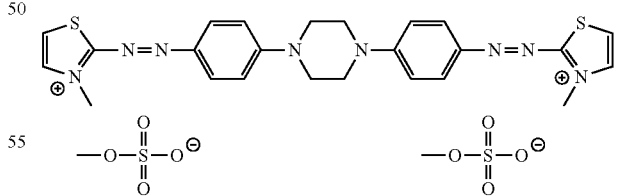

The dye DZ 1 was synthesized using a method as described in GB 1186753. Diethyl sulfate was used as the quaternizing agent.

Dyeing Examples

Formulations

The following coloring creams were prepared (all information in wt %, of active substance)

|  | Example 1 | Example 2 |
|---|---|---|
| Cetearyl alcohol (C$_{16}$/C$_{18}$ fatty alcohol) | 1.0 | 1.0 |
| Coconut alcohol (C$_{12}$/C$_{18}$ fatty alcohol) | 1.0 | 1.0 |
| Methyl paraben | 0.1 | 0.1 |
| Propylparaben | 0.1 | 0.1 |
| Ceteareth-12 | 3.0 | — |
| Ceteareth-20 | 3.0 | — |
| Sodium laureth-5 carboxylate | — | 1.0 |
| DZ 1 (inventive) | 1.0 | 1.0 |
| Ammonium sulfate | 1.0 | 1.0 |
| Water | Up to 100 | Up to 100 |

The fatty alcohols and preservatives were fused together with the surfactants. This melt was emulsified with hot water, after which the dye—which had been previously dissolved in a small amount of hot water—was added. The ammonium sulfate solution was then added. The indicated pH value was set using ammoniac (as well as citric acid, as necessary), and water was then used to fill to 100 g.

Dyeing 1.8 g of the coloring cream was applied to an approximately 6 cm-long strand of human hair (Kerling European natural hair, 80% grayed) and left there for 30 minutes at 30° C. At the end of the exposure time, the hair was rinsed out, washed with a common hair wash, and then dried. After drying, the coloration and the color intensity of the strands was assessed visually under the daylight lamp.

|  | Formulation | pH value | Color nuance | Color intensity |
|---|---|---|---|---|
| Example 1 | DZ 1 with ceteareth-12 and ceteareth-20 | 9.5 | grayish blue | +++ |
| Example 2 | DZ 1 with sodium laureth-5 carboxylate | 9.5 | dark blue | ++++ |

Color intensity:
+ = poor
+++ = moderate
+++++ = very good

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for dyeing keratin fibers, the agent comprising, in a cosmetic carrier, (a) at least one direct dye of formula (I),

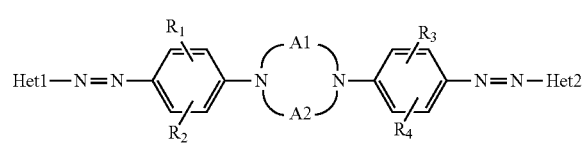

(I)

where

Het 1, Het 2 independently of one another, stand for one of the structures (II), (III), (IV), (V), (VI), or (VII),

(II)

(III)

(IV)

(V)

(VI)

(VII)

R$^1$, R$^3$ independently of one another, stand for a hydrogen atom, a C$_1$-C$_6$ alkyl group, a halogen atom from the group of chlorine, bromine, fluorine, or iodine, for a C$_1$-C$_6$ alkoxy group, or for a nitro group, R$^2$, R$^4$ independently of one another, stand for a hydrogen atom, a C$_1$-C$_6$ alkyl group, a halogen atom from the group of chlorine, bromine, fluorine, or iodine, for a C$_1$-C$_6$ alkoxy group, or for a nitro group, R$^5$, R$^8$ each independently of one another, stand for a C$_1$-C$_6$ alkyl group or for a C$_2$-C$_6$ alkenyl group, R$^6$, R$^7$ each independently of one another, stand for a hydrogen atom, a C$_1$-C$_6$ alkyl group, a halogen atom from the group of chlorine, bromine, fluorine, or iodine, for a C$_1$-C$_6$ alkoxy group, or for a nitro group, A1, A2 independently of one another, stand for a grouping of the formulas (VIII) or (IX),

*—(CH₂)ₙ-*   (VIII)

*—(CH₂)ₘ—O—(CH₂)ₚ-*   (IX)

n stands for an integer from 2 to 6, m, p each independently of one another, stand for the numbers 2 or 3, X— stands for a physiologically acceptable anion, chloride, bromide, iodide, methyl sulfate, methyl sulfonate, p-toluene sulfonate, acetate, hydrogen sulfate, ½ sulfate, or ½ tetrachlorozincate; and wherein the agent comprises, with respect to the total weight of the agent, one or more direct dyes (a) of formula (I) in a total quantity from about 0.01 to about 4.5 wt %.

2. The agent as set forth in claim 1, wherein the agent comprises at least one direct dye of the general formula (I), in which Het 1, Het 2 independently of one another, stand for one of the structures (II), (III), or (IV)

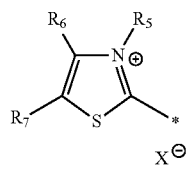
(II)

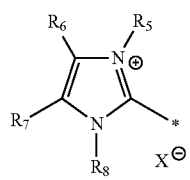
(III)

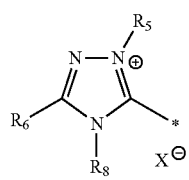
(IV)

3. The agent as set forth in claim 1, wherein the agent comprises at least one direct dye of general formula (I), in which R¹, R³ independently of one another, stand for a hydrogen atom, a $C_1$-$C_6$ alkyl group, or for a $C_1$-$C_6$ alkoxy group.

4. The agent as set forth in claim 1, wherein the agent comprises at least one direct dye of general formula (I), in which R², R⁴ independently of one another, stand for a hydrogen atom, a $C_1$-$C_6$ alkyl group, or for a $C_1$-$C_6$ alkoxy group.

5. The agent as set forth in claim 1, wherein the agent comprises at least one direct dye of general formula (I), in which R⁵, R⁸ each independently of one another, stand for a $C_1$-$C_6$ alkyl group, and R⁶, R⁷ each independently of one another, stand for a hydrogen atom, a $C_1$-$C_6$ alkyl group, or for a $C_1$-$C_6$ alkoxy group.

6. The agent as set forth in claim 1, wherein the agent comprises at least one direct dye of general formula (I), in which A1, A2 both stand for a grouping of formula (VIII),

*—(CH₂)ₙ-*   (VII), where n stands for the number 2 or 3.

7. The agent as set forth in claim 1, wherein the agent comprises at least one direct dye of general formula (I), which is selected from:

salts of 3-methyl-2-{2-[4-(4-{4-[2-(3-methyl-1,3-thiazol-3-ium-2-yl)diazen-1-yl]phenyl}piperazin-1-yl)phenyl]diazen-1-yl}-1,3-thiazol-3-ium, salts of 3-ethyl-2-{2-[4-(4-{4-[2-(3-ethyl-1,3-thiazol-3-ium-2-yl)diazen-1-yl]phenyl}piperazin-1-yl)phenyl]diazen-1-yl}-1,3-thiazol-3-ium, salts of 3-methyl-2-{2-[3-methyl-4-(4-{2-methyl-4-[2-(3-methyl-1,3-thiazol-3-ium-2-yl)diazen-1-yl]phenyl}piperazin-1-yl)phenyl]diazen-1-yl}-1,3-thiazol-3-ium, salts of 3-ethyl-2-{2-[4-(4-{4-[2-(3-ethyl-1,3-thiazol-3-ium-2-yl)diazen-1-yl]-2-methylphenyl}piperazin-1-yl)-3-methylphenyl]diazen-1-yl}-1,3-thiazol-3-ium, salts of 3-methyl-2-{2-[2-methyl-4-(4-{3-methyl-4-[2-(3-methyl-1,3-thiazol-3-ium-2-yl)diazen-1-yl]phenyl}piperazin-1-yl)phenyl]diazen-1-yl}-1,3-thiazol-3-ium, salts of 3-ethyl-2-{2-[4-(4-{4-[2-(3-ethyl-1,3-thiazol-3-ium-2-yl)diazen-1-yl]-3-methylphenyl}piperazin-1-yl)-2-methylphenyl]diazen-1-yl}-1,3-thiazol-3-ium, salts of 2-{2-[3-methoxy-4-(4-{2-methoxy-4-[2-(3-methyl-1,3-thiazol-3-ium-2-yl)diazen-1-yl]phenyl}piperazin-1-yl)phenyl]diazen-1-yl}-3-methyl-1,3-thiazol-3-ium, salts of 3-ethyl-2-{2-[4-(4-{4-[2-(3-ethyl-1,3-thiazol-3-ium-2-yl)diazen-1-yl]-2-methoxyphenyl}piperazin-1-yl)-3-methoxyphenyl]diazen-1-yl}-1,3-thiazol-3-ium, salts of 2-{2-[2-methoxy-4-(4-{3-methoxy-4-[2-(3-methyl-1,3-thiazol-3-ium-2-yl)diazen-1-yl]phenyl}piperazin-1-yl)phenyl]diazen-1-yl}-3-methyl-1,3-thiazol-3-ium, salts of 3-ethyl-2-{2-[4-(4-{4-[2-(3-ethyl-1,3-thiazol-3-ium-2-yl)diazen-1-yl]-3-methoxyphenyl}piperazin-1-yl)-2-methoxyphenyl]diazen-1-yl}-1,3-thiazol-3-ium, salts of 2-{2-[4-(4-{2,5-dimethyl-4-[2-(3-methyl-1,3-thiazol-3-ium-2-yl)diazen-1-yl]phenyl}piperazin-1-yl)-2,5-dimethylphenyl]diazen-1-yl}-3-methyl-1,3-thiazol-3-ium, salts of 3-ethyl-2-{2-[4-(4-{4-[2-(3-ethyl-1,3-thiazol-3-ium-2-yl)diazen-1-yl]-2,5-dimethylphenyl}piperazin-1-yl)-2,5-dimethylphenyl]diazen-1-yl}-1,3-thiazol-3-ium, salts of 2-{2-[4-(4-{4-[2-(1,3-dimethyl-1H-imidazol-3-ium-2-yl)diazen-1-yl]phenyl}piperazin-1-yl)phenyl]diazen-1-yl}-1,3-dimethyl-1H-imidazol-3-ium, salts of 2-{2-[4-(4-{4-[2-(1,3-diethyl-1H-imidazol-3-ium-2-yl)diazen-1-yl]phenyl}piperazin-1-yl)phenyl]diazen-1-yl}-1,3-diethyl-1H-imidazol-3-ium, salts of 2-{2-[4-(4-{4-[2-(1,3-dimethyl-1H-imidazol-3-ium-2-yl)diazen-1-yl]-2-methylphenyl}piperazin-1-yl)-3-methylphenyl]diazen-1-yl}-1,3-dimethyl-1H-imidazol-3-ium, salts of 2-{2-[4-(4-{4-[2-(1,3-diethyl-1H-imidazol-3-ium-2-yl)diazen-1-yl]-2-methylphenyl}piperazin-1-yl)-3-methylphenyl]diazen-1-yl}-1,3-diethyl-1H-imidazol-3-ium, salts of 2-{2-[4-(4-{4-[2-(1,3-dimethyl-1H-imidazol-3-ium-2-yl)diazen-1-yl]-3-methylphenyl}piperazin-1-yl)-2-methylphenyl]diazen-1-yl}-1,3-dimethyl-1H-imidazol-3-ium, salts of 2-{2-[4-(4-{4-[2-(1,3-diethyl-1H-imidazol-3-ium-2-yl)diazen-1-yl]-3-methylphenyl}piperazin-1-yl)-2-methylphenyl]diazen-1-yl}-1,3-diethyl-1H-imidazol-3-ium, salts of 2-{2-[4-(4-{4-[2-(1,3-dimethyl-1H-imidazol-3-ium-2-yl)diazen-1-yl]-2-methoxyphenyl}piperazin-1-yl)-3-methoxyphenyl]diazen-1-yl}-1,3-dimethyl-1H-imidazol-3-ium, salts of 2-{2-[4-(4-{4-[2-(1,3-diethyl-1H-imidazol-3-ium-2-yl)diazen-1-yl]-2-methoxyphenyl}piperazin-1-yl)-3-methoxyphenyl]diazen-1-yl}-1,3-diethyl-1H-imidazol-3-ium, salts of 2-{2-[4-(4-{4-[2-(1,3-dimethyl-1H-imidazol-3-ium-2-yl)diazen-1-yl]-3-methoxyphenyl}piperazin-1-yl)-2-methoxyphenyl]diazen-1-yl}-1,3-dimethyl-1H-imidazol-3-ium, salts of 2-{2-[4-(4-{4-[2-(1,3-diethyl-1H-imidazol-3-ium-2-yl)diazen-1-yl]-3-methoxyphenyl}piperazin-1-yl)-2-methoxyphenyl]diazen-1-yl}-1,3-diethyl-1H-imidazol-3-ium, salts of 2-{2-[4-(4-{4-[2-(1,3-dimethyl-1H-imidazol-3-ium-2-yl)diazen-1-yl]-2,5-dimethylphenyl}piperazin-1-yl)-2,5-dimethylphenyl]diazen-1-yl}-1,3-dimethyl-1H-imidazol-3-ium, salts of 2-{2-[4-(4-{4-[2-(1,3-diethyl-1H-imidazol-3-ium-2-yl)diazen-1-yl]-2,5-dimethylphenyl}piperazin-1-yl)-2,5-dimethylphenyl]diazen-1-yl}-1,3-diethyl-1H-imidazol-3-ium, salts of 5-{2-[4-(4-{4-[2-(1,4-dimethyl-1H-1,2,4-triazol-4-ium-5-yl)diazen-1-yl]phenyl}piperazin-1-yl)phenyl]diazen-1-yl}-1,4-dimethyl-1H-1,2,4-triazol-4-ium, salts of 5-{2-[4-(4-{4-[2-(1,4-diethyl-1H-1,2,4-triazol-4-ium-5-yl)diazen-1-yl]phenyl}piperazin-1-yl)phenyl]diazen-1-yl}-1,4-diethyl-1H-1,2,4-triazol-4-ium, salts of 5-{2-[4-(4-{4-[2-(1,4-dimethyl-1H-1,2,4-triazol-4-ium-5-yl)diazen-1-yl]-2-methylphenyl}piperazin-1-yl)-3-methylphenyl]diazen-1-yl}-1,4-dimethyl-1H-1,2,4-triazol-4-ium, salts of 5-{2-[4-(4-{4-[2-(1,4-diethyl-1H-1,2,4-triazol-4-ium-5-yl)diazen-1-yl]-2-methylphenyl}piperazin-1-yl)-3-methylphenyl]diazen-1-yl}-1,4-diethyl-1H-1,2,4-triazol-4-ium, salts of 5-{2-[4-(4-{4-[2-(1,4-dimethyl-1H-1,2,4-triazol-4-ium-5-yl)diazen-1-yl]-3-methylphenyl}piperazin-1-yl)-2-methylphenyl]diazen-1-yl}-1,4-dimethyl-1H-1,2,4-triazol-4-ium, salts of 5-{2-[4-(4-{4-[2-(1,4-diethyl-1H-1,2,4-triazol-4-ium-5-yl)diazen-1-yl]-3-methylphenyl}piperazin-1-yl)-2-methylphenyl]diazen-1-yl}-1,4-diethyl-1H-1,2,4-triazol-4-ium, salts of 5-{2-[4-(4-{4-[2-(1,4-dimethyl-1H-1,2,4-triazol-4-ium-5-yl)diazen-1-yl]-2-methoxyphenyl}piperazin-1-yl)-3-methoxyphenyl]diazen-1-yl}-1,4-dimethyl-1H-1,2,4-triazol-4-ium, salts of 5-{2-[4-(4-{4-[2-(1,4-diethyl-1H-1,2,4-triazol-4-ium-5-yl)diazen-1-yl]-2-methoxyphenyl}piperazin-1-yl)-3-methoxyphenyl]diazen-1-yl}-1,4-diethyl-1H-1,2,4-triazol-4-ium, salts of 5-{2-[4-(4-{4-[2-(1,4-dimethyl-1H-1,2,4-triazol-4-ium-5-yl)diazen-1-yl]-3-methoxyphenyl}piperazin-1-yl)-2-methoxyphenyl]diazen-1-yl}-1,4-dimethyl-1H-1,2,4-triazol-4-ium, salts of 5-{2-[4-(4-{4-[2-(1,4-diethyl-1H-1,2,4-triazol-4-ium-5-yl)diazen-1-yl]-3-methoxyphenyl}piperazin-1-yl)-2-methoxyphenyl]diazen-1-yl}-1,4-diethyl-1H-1,2,4-triazol-4-ium, salts of 5-{2-[4-(4-{4-[2-(1,4-dimethyl-1H-1,2,4-triazol-4-ium-5-yl)diazen-1-yl]-2,5-dimethylphenyl}piperazin-1-yl)-2,5-dimethylphenyl]diazen-1-yl}-1,4-dimethyl-1H-1,2,4-triazol-4-ium, salts of 5-{2-[4-(4-{4-[2-(1,4-diethyl-1H-1,2,4-triazol-4-ium-5-yl)diazen-1-yl]-2,5-dimethyl-phenyl}piperazin-1-yl)-2,5-dimethylphenyl]diazen-1-yl}-1,4-diethyl-1H-1,2,4-triazol-4-ium, salts of 3-methyl-2-{2-[4-(5-{4-[2-(3-methyl-1,3-thiazol-3-ium-2-yl)diazen-1-yl]phenyl}-1,5-diazocan-1-yl)phenyl]diazen-1-yl}-1,3-thiazol-3-ium, salts of 3-ethyl-2-{2-[4-(5-{4-[2-(3-ethyl-1,3-thiazol-3-ium-2-yl)diazen-1-yl]phenyl}-1,5-diazocan-1-yl)phenyl]diazen-1-yl}-1,3-thiazol-3-ium, salts of 3-methyl-2-{2-[3-methyl-4-(5-{2-methyl-4-[2-(3-methyl-1,3-thiazol-3-ium-2-yl)diazen-1-yl]phenyl}-1,5-diazocan-1-yl)phenyl]diazen-1-yl}-1,3-thiazol-3-ium, salts of 3-ethyl-2-{2-[4-(5-{4-[2-(3-ethyl-1,3-thiazol-3-ium-2-yl)diazen-1-yl]-2-methylphenyl}-1,5-diazocan-1-yl)-3-methylphenyl]diazen-1-yl}-1,3-thiazol-3-ium, salts of 3-methyl-2-{2-[2-methyl-4-(5-{3-methyl-4-[2-(3-methyl-1,3-thiazol-3-ium-2-yl)diazen-1-yl]phenyl}-1,5-diazocan-1-yl)phenyl]diazen-1-yl}-1,3-thiazol-3-ium, salts of 3-ethyl-2-{2-[4-(5-{4-[2-(3-ethyl-1,3-thiazol-3-ium-2-yl)diazen-1-yl]-3-methylphenyl}-1,5-diazocan-1-yl)-2-methylphenyl]diazen-1-yl}-1,3-thiazol-3-ium, salts of 2-{2-[3-methoxy-4-(5-{2-methoxy-4-[2-(3-methyl-1,3-thiazol-3-ium-2-yl)diazen-1-yl]phenyl}-1,5-diazocan-1-yl)phenyl]diazen-1-yl}-3-methyl-1,3-thiazol-3-ium, salts of 3-ethyl-2-{2-[4-(5-{4-[2-(3-ethyl-1,3-thiazol-3-ium-2-yl)diazen-1-yl]-2-methoxyphenyl}-1,5-diazocan-1-yl)-3-methoxyphenyl]diazen-1-yl}-1,3-thiazol-3-ium, salts of 2-{2-[2-methoxy-4-(5-{3-methoxy-4-[2-(3-methyl-1,3-thiazol-3-ium-2-yl)diazen-1-yl]phenyl}-1,5-diazocan-1-yl)phenyl]diazen-1-yl}-3-methyl-1,3-thiazol-3-ium, salts of 3-ethyl-2-{2-[4-(5-{4-[2-(3-ethyl-1,3-thiazol-3-ium-2-yl)diazen-1-yl]-3-methoxyphenyl}-1,5-diazocan-1-yl)-2-methoxyphenyl]diazen-1-yl}-1,3-thiazol-3-ium, salts of 2-{2-[4-(5-{2,5-dimethyl-4-[2-(3-methyl-1,3-thiazol-3-ium-2-yl)diazen-1-yl]phenyl}-1,5-diazocan-1-yl)-2,5-dimethylphenyl]diazen-1-yl}-3-methyl-1,3-thiazol-3-ium, salts of 3-ethyl-2-{2-[4-(5-{4-[2-(3-ethyl-1,3-thiazol-3-ium-2-yl)diazen-1-yl]-2,5-dimethylphenyl}-1,5-diazocan-1-yl)-2,5-dimethylphenyl]diazen-1-yl}-1,3-thiazol-3-ium, salts of 2-{2-[4-(5-{4-[2-(1,3-dimethyl-1H-imidazol-3-ium-2-yl)diazen-1-yl]phenyl}-1,5-diazocan-1-yl)phenyl]diazen-1-yl}-1,3-dimethyl-1H-imidazol-3-ium, salts of 2-{2-[4-(5-{4-[2-(1,3-diethyl-1H-imidazol-3-ium-2-yl)diazen-1-yl]phenyl}-1,5-diazocan-1-yl)phenyl]diazen-1-yl}-1,3-diethyl-1H-imidazol-3-ium, salts of 2-{2-[4-(5-{4-[2-(1,3-dimethyl-1H-imidazol-3-ium-2-yl)diazen-1-yl]-2-methylphenyl}-1,5-diazocan-1-yl)-3-methylphenyl]diazen-1-yl}-1,3-dimethyl-1H-imidazol-3-ium, salts of 2-{2-[4-(5-{4-[2-(1,3-diethyl-1H-imidazol-3-ium-2-yl)diazen-1-yl]-2-methylphenyl}-1,5-diazocan-1-yl)-3-methylphenyl]diazen-1-yl}-1,3-diethyl-1H-imidazol-3-ium, salts of 2-{2-[4-(5-{4-[2-(1,3-dimethyl-1H-imidazol-3-ium-2-yl)diazen-1-yl]-3-methylphenyl}-1,5-diazocan-1-yl)-2-methylphenyl]diazen-1-yl}-1,3-dimethyl-1H-imidazol-3-ium, salts of 2-{2-[4-(5-{4-[2-(1,3-diethyl-1H-imidazol-3-ium-2-yl)diazen-1-yl]-3-methylphenyl}-1,5-diazocan-1-yl)-2-methylphenyl]diazen-1-yl}-1,3-diethyl-1H-imidazol-3-ium, salts of 2-{2-[4-(5-{4-[2-(1,3-dimethyl-1H-imidazol-3-ium-2-yl)diazen-1-yl]-2-methoxyphenyl}-1,5-diazocan-1-yl)-3-methoxyphenyl]diazen-1-yl}-1,3-dimethyl-1H-imidazol-3-ium, salts of 2-{2-[4-(5-{4-[2-(1,3-diethyl-1H-imidazol-3-ium-2-yl)diazen-1-yl]-2-methoxyphenyl}-1,5-diazocan-1-yl)-3-methoxyphenyl]diazen-1-yl}-1,3-diethyl-1H-imidazol-3-ium, salts of 2-{2-[4-(5-{4-[2-(1,3-dimethyl-1H-imidazol-3-ium-2-yl)diazen-1-yl]-3-methoxyphenyl}-1,5-diazocan-1-yl)-2-methoxyphenyl]diazen-1-yl}-1,3-dimethyl-1H-imidazol-3-ium, salts of 2-{2-[4-(5-{4-[2-(1,3-diethyl-1H-imidazol-3-ium-2-yl)diazen-1-yl]-3-methoxyphenyl}-1,5-diazocan-1-yl)-2-methoxyphenyl]diazen-1-yl}-1,3-diethyl-1H-imidazol-3-ium, salts of 2-{2-[4-(5-{4-[2-(1,3-dimethyl-1H-imidazol-3-ium-2-yl)diazen-1-yl]-2,5-dimethylphenyl}-1,5-diazocan-1-yl)-2,5-dimethylphenyl]diazen-1-yl}-1,3-dimethyl-1H-imidazol-3-ium, salts of 2-{2-[4-(5-{4-[2-(1,3-diethyl-1H-imidazol-3-ium-2-yl)diazen-1-yl]-2,5-dimethylphenyl}-1,5-diazocan-1-yl)-2,5-dimethylphenyl]diazen-1-yl}-1,3-diethyl-1H-imidazol-3-ium, salts of 5-{2-[4-(5-{4-[2-(1,4-dimethyl-1H-1,2,4-triazol-4-ium-5-yl)diazen-1-yl]phenyl}-1,5-diazocan-1-yl)phenyl]diazen-1-yl}-1,4-dimethyl-1H-1,2,4-triazol-4-ium, salts of 5-{2-[4-(5-{4-[2-(1,4-diethyl-1H-1,2,4-triazol-4-ium-5-yl)diazen-1-yl]phenyl}-1,5-diazocan-1-yl)phenyl]diazen-1-yl}-1,4-diethyl-1H-1,2,4-triazol-4-ium, salts of 5-{2-[4-(5-{4-[2-(1,4-dimethyl-1H-1,2,4-triazol-4-ium-5-yl)diazen-1-yl]-2-methylphenyl}-1,5-diazocan-1-yl)-3-methylphenyl]diazen-1-yl}-1,4-dimethyl-1H-1,2,4-triazol-4-ium, salts of 5-{2-[4-(5-{4-[2-(1,4-diethyl-1H-1,2,4-triazol-4-ium-5-yl)diazen-1-yl]-2-methylphenyl}-1,5-diazocan-1-yl)-3-methylphenyl]diazen-1-yl}-1,4-diethyl-1H-1,2,4-triazol-4-ium, salts of 5-{2-[4-(5-{4-[2-(1,4-dimethyl-1H-1,2,4-triazol-4-ium-5-yl)diazen-1-yl]-3-methylphenyl}-1,5-diazocan-1-yl)-2-methylphenyl]diazen-1-yl}-1,4-dimethyl-1H-1,2,4-triazol-4-ium, salts of 5-{2-[4-(5-{4-[2-(1,4-diethyl-1H-1,2,4-triazol-4-ium-5-yl)diazen-1-yl]-3-methylphenyl}-1,5-diazocan-1-yl)-2-methylphenyl]diazen-1-yl}-1,4-diethyl-1H-1,2,4-triazol-4-ium, salts of 5-{2-[4-(5-{4-[2-(1,4-dimethyl-1H-1,2,4-triazol-4-ium-5-yl)diazen-1-yl]-2-methoxy-phenyl}-1,5-diazocan-1-yl)-3-methoxyphenyl]diazen-1-yl}-1,4-dimethyl-1H-1,2,4-triazol-4-ium, salts of 5-{2-[4-(5-{4-[2-(1,4-diethyl-1H-1,2,4-triazol-4-ium-5-yl)diazen-1-yl]-2-methoxyphenyl}-1,5-diazocan-1-yl)-3-methoxyphenyl]diazen-1-yl}-1,4-diethyl-1H-1,2,4-triazol-4-ium, salts of 5-{2-[4-(5-{4-[2-(1,4-dimethyl-1H-1,2,4-triazol-4-ium-5-yl)diazen-1-yl]-3-methoxy-phenyl}-1,5-diazocan-1-yl)-2-methoxyphenyl]diazen-1-yl}-1,4-dimethyl-1H-1,2,4-triazol-4-ium, salts of 5-{2-[4-(5-{4-[2-(1,4-diethyl-1H-1,2,4-triazol-4-ium-5-yl)diazen-1-yl]-3-methoxyphenyl}-1,5-diazocan-1-yl)-2-methoxyphenyl]diazen-1-yl}-1,4-diethyl-1H-1,2,4-triazol-4-ium, salts of 5-{2-[4-(5-{4-[2-(1,4-dimethyl-1H-1,2,4-triazol-4-ium-5-yl)diazen-1-yl]-2,5-dimethyl-phenyl}-1,5-diazocan-1-yl)-2,5-dimethylphenyl]diazen-1-yl}-1,4-dimethyl-1H-1,2,4-triazol-4-ium, and/or salts of 5-{2-[4-(5-{4-[2-(1,4-diethyl-1H-1,2,4-triazol-4-ium-5-yl)diazen-1-yl]-2,5-dimethyl-phenyl}-1,5-diazocan-1-yl)-2,5-dimethylphenyl]diazen-1-yl}-1,4-diethyl-1H-1,2,4-triazol-4-ium.

8. The agent as set forth in claim 1, wherein the agent comprises, with respect to the total weight of the agent, one or more direct dyes (a) of formula (I) in a total quantity from about 0.05 to about 2.8 wt %.

9. The agent as set forth in claim 1, wherein the agent comprises, with respect to the total weight of the agent, one or more direct dyes (a) of formula (I) in a total quantity from about 0.1 to about 2.2 wt %.

10. An agent for dyeing keratin fibers, the agent comprising, in a cosmetic carrier, (a) at least one direct dye of formula (I),

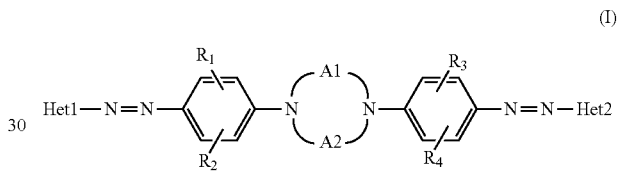

where

Het 1, Het 2 independently of one another, stand for one of the structures (II), (III), (IV), (V), (VI), or (VII),

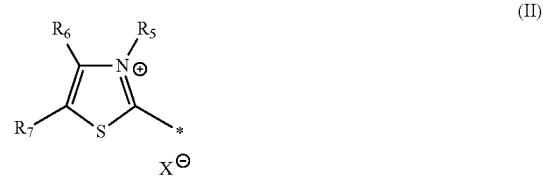

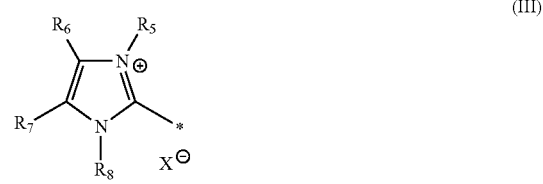

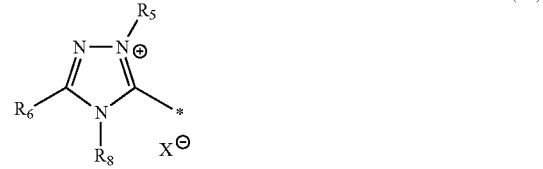

-continued

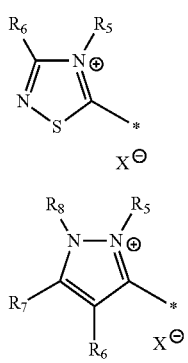

R¹, R³ independently of one another, stand for a hydrogen atom, a $C_1$-$C_6$ alkyl group, a halogen atom from the group of chlorine, bromine, fluorine, or iodine, for a $C_1$-$C_6$ alkoxy group, or for a nitro group, R², R⁴ independently of one another, stand for a hydrogen atom, a $C_1$-$C_6$ alkyl group, a halogen atom from the group of chlorine, bromine, fluorine, or iodine, for a $C_1$-$C_6$ alkoxy group, or for a nitro group, R⁵, R⁸ each independently of one another, stand for a $C_1$-$C_6$ alkyl group or for a $C_2$-$C_6$ alkenyl group, R⁶, R⁷ each independently of one another, stand for a hydrogen atom, a $C_1$-$C_6$ alkyl group, a halogen atom from the group of chlorine, bromine, fluorine, or iodine, for a $C_1$-$C_6$ alkoxy group, or for a nitro group, A1, A2 independently of one another, stand for a grouping of the formulas (VIII) or (IX),

*—$(CH_2)_n$—* (VIII)

*—$(CH_2)_m$—O—$(CH_2)_p$—* (IX)

n stands for an integer from 2 to 6, m, p each independently of one another, stand for the numbers 2 or 3, X— stands for a physiologically acceptable anion, chloride, bromide, iodide, methyl sulfate, methyl sulfonate, p-toluene sulfonate, acetate, hydrogen sulfate, ½ sulfate, or ½ tetrachlorozincate; and an oxidizing agent.

11. The agent as set forth in claim 10, wherein the agent comprises, with respect to the total weight of the agent, one or more direct dyes (a) of formula (I) in a total quantity from about 0.01 to about 4.5 wt %.

12. The agent as set forth in claim 10, wherein the agent comprises at least one anionic surfactant (b) from the group of the ether carboxylic acids of formula (B1)

R—O—$(CH_2$—$CH_2O)_x$—$CH_2$—COOM (B1), where

R stands for a linear alkyl group with 8 to 30 C atoms, x stands for an integer from 0 to 16, M stands for hydrogen, a metal, an alkali metal, sodium, potassium, lithium, an alkaline earth metal, ½ magnesium, ½ calcium, ½ zinc, or an ammonium ion ($NH_4^+$).

13. The agent as set forth in claim 10, wherein the oxidizing agent comprises hydrogen peroxide and/or at least one persulfate; and/or wherein the agent comprises, with respect to the total weight of the agent, about 0.5 to about 12.5 wt % hydrogen peroxide; and/or wherein the at least one persulfate is selected from the group of ammonium peroxodisulfate, potassium peroxodisulfate, and sodium peroxodisulfate.

14. The agent as set forth in claim 13, wherein the agent comprises, with respect to the total weight of the agent, about 0.2 to about 13.5 wt % ammonium peroxodisulfate about 0.5 to about 4.5 wt % potassium peroxodisulfate, and about 0.2 to about 1.8 wt % sodium peroxodisulfate.

15. The agent as set forth in claim 13, wherein the agent comprises, with respect to the total weight of the agent, about 2.5 to about 10 wt % hydrogen peroxide.

16. The agent as set forth in claim 13, wherein the agent comprises, with respect to the total weight of the agent, about 0.5 to about 1.5 wt % ammonium peroxodisulfate about 1.5 to about 2.5 wt % potassium peroxodisulfate, and about 0.4 to about 0.8 wt % sodium peroxodisulfate.

17. An agent for dyeing keratin fibers, the agent comprising, in a cosmetic carrier, (a) at least one direct dye of formula (I),

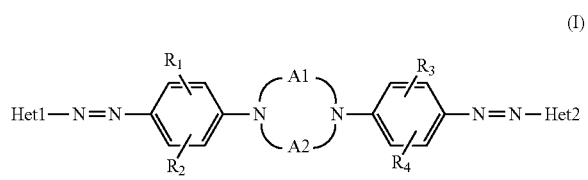

where

Het 1, Het 2 independently of one another, stand for one of the structures (II), (III), (IV), (V), (VI), or (VII),

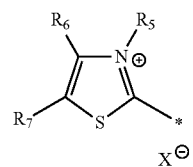

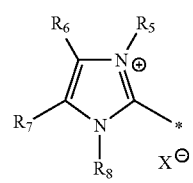

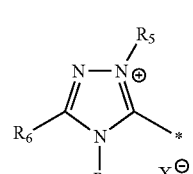

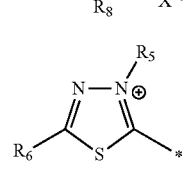

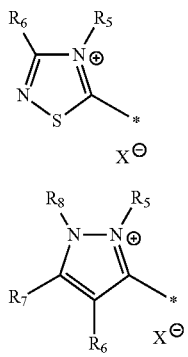

R¹, R³ independently of one another, stand for a hydrogen atom, a $C_1$-$C_6$ alkyl group, a halogen atom from the group of chlorine, bromine, fluorine, or iodine, for a $C_1$-$C_6$ alkoxy group, or for a nitro group, R², R⁴ independently of one another, stand for a hydrogen atom, a $C_1$-$C_6$ alkyl group, a halogen atom from the group of chlorine, bromine, fluorine, or iodine, for a $C_1$-$C_6$ alkoxy group, or for a nitro group, R⁵, R⁸ each independently of one another, stand for a $C_1$-$C_6$ alkyl group or for a $C_2$-$C_6$ alkenyl group, R⁶, R⁷ each independently of one another, stand for a hydrogen atom, a $C_1$-$C_6$ alkyl group, a halogen atom from the group of chlorine, bromine, fluorine, or iodine, for a $C_1$-$C_6$ alkoxy group, or for a nitro group, A1, A2 independently of one another, stand for a grouping of the formulas (VIII) or (IX), $$*-(CH_2)n-* \tag{VIII}$$

$$*-(CH_2)m\text{-}O\text{-}(CH_2)p-* \tag{IX}$$

n stands for an integer from 2 to 6, m, p each independently of one another, stand for the numbers 2 or 3, X— stands for a physiologically acceptable anion, chloride, bromide, iodide, methyl sulfate, methyl sulfonate, p-toluene sulfonate, acetate, hydrogen sulfate, ½ sulfate, or ½ tetrachlorozincate; and one or more anionic surfactants.

18. The agent as set forth in claim 17, wherein the weight ratio of all of the anionic surfactants of formula (B1) contained in the agent to the total quantity of the anionic surfactants contained in the agent is about 0.5 to about 0.9, with the anionic surfactants of formula (B1) being the following surfactants $$R\text{—}O\text{—}(CH_2\text{—}CH_2O)_x\text{—}CH_2\text{—}COOM \tag{B1},$$

where

R is equal to a linear alkyl group with 8 to 30 C atoms, x is equal to an integer from 0 to 16, M is equal to hydrogen, a metal, an alkali metal, sodium, potassium, lithium, an alkaline earth metal, ½ magnesium, ½ calcium, ½ zinc, or an ammonium ion ($NH_4^+$).

19. The agent as set forth in claim 17, wherein the agent comprises, with respect to the total weight of the agent, one or more anionic surfactants (b) in a total quantity from about 0.1 to about 3.1 wt %.

20. The agent as set forth in claim 17, wherein the agent comprises, with respect to the total weight of the agent, the one or more anionic surfactants in a total quantity from about 0.05 to about 9.5 wt %; and/or wherein at least one anionic surfactant of the one or more anionic surfactants is selected from:

linear and branched fatty acids with 8 to 30 C atoms, ether carboxylic acids of the formula R—O—($CH_2$—$CH_2O)_x$—$CH_2$—COOM, in which R stands for a linear alkyl group with 8 to 30 C atoms, x stands for an integer from 0 to 16, M stands for hydrogen, a metal, an alkali metal, sodium, potassium, lithium, an alkaline earth metal, ½ magnesium, ½ calcium, ½ zinc, or an ammonium ion ($NH_4^+$), acyl sarcosides with 8 to 24 C-atoms in the acyl group, acyl taurides with 8 to 24 C-atoms in the acyl group, acyl isethionates with 8 to 24 C-atoms in the acyl group, obtained through esterification of $C_8$-$C_{24}$ fatty acids with the sodium salt of 2-hydroxyethane sulfonic acid (isethionic acid), amide ether carboxylic acids, R¹—CO—NR²—$CH_2CH_2$—O—($CH_2CH_2O)_y CH_2 COOM$, where R¹ stands for a $C_2$-$C_{30}$ alkyl group, x stands for an integer from 1 to 20, R² stands for hydrogen, methyl, ethyl, propyl, isopropyl, n-butyl, t-butyl, or iso-butyl residue, and M stands for hydrogen, a metal, an alkali metal, sodium, potassium, lithium, an alkaline earth metal, ½ magnesium, ½ calcium, ½ zinc, or an ammonium ion ($NH_4^+$).

* * * * *